(12) United States Patent
Singh et al.

(10) Patent No.: US 6,483,959 B1
(45) Date of Patent: Nov. 19, 2002

(54) WAVEGUIDE STRUCTURES

(75) Inventors: Kirat Singh, Hadfield (GB); Nicholas John Goddard, Warrington (GB)

(73) Assignee: The University of Manchester Institute of Science and Technology, Manchester (GB)

(\*) Notice: Subject to any disclaimer, the term of this patent is extended or adjusted under 35 U.S.C. 154(b) by 0 days.

(21) Appl. No.: 09/622,698

(22) PCT Filed: Feb. 24, 1999

(86) PCT No.: PCT/GB99/00399

§ 371 (c)(1),
(2), (4) Date: Oct. 19, 2000

(87) PCT Pub. No.: WO99/44042

PCT Pub. Date: Sep. 2, 2000

(30) Foreign Application Priority Data

Feb. 24, 1998 (GB) .............................................. 9803704

(51) Int. Cl.⁷ ................................................. G02B 6/00
(52) U.S. Cl. .............................. 385/12; 385/5; 385/141
(58) Field of Search ............................ 385/12, 5, 141; 372/64

(56) References Cited

U.S. PATENT DOCUMENTS

| | | | | |
|---|---|---|---|---|
| 5,120,131 A | \* | 6/1992 | Lukosz | 356/351 |
| 5,485,277 A | \* | 1/1996 | Foster | 356/445 |
| 5,521,702 A | \* | 5/1996 | Salamon et al. | 356/244 |
| 6,330,387 B1 | \* | 12/2001 | Salamon et al. | 385/129 |

FOREIGN PATENT DOCUMENTS

EP 0 679 881 A1 11/1995

OTHER PUBLICATIONS

R. Cush, J.M. Cronin, W.J. Stewart, C.H. Maule, J. Molloy, N.J. Goddard, "The resonant mirror: a novel optical biosensor for direct sensing of biomolecular interactions Part I: Principle of operation and associated instrumentation", *Biosensors & Bioelectronics*, 8 (1993), pp. 347–353.

(List continued on next page.)

*Primary Examiner*—Scott J. Sugarman
*Assistant Examiner*—M. Hasan
(74) *Attorney, Agent, or Firm*—Woodard, Emhardt, Naughton, Moriarty & McNett

(57) ABSTRACT

A waveguide structure comprising a medium disposed of a sensing layer (21), a second layer of material (22) having a refractive index greater than that of the medium, and a substrate (24). The structure defines a waveguide capable of supporting an optical mode confined in a sensing layer. The medium is adapted for performing chemical or biological reactions within the medium which will result in a change of an optical property of the sensing layer of the waveguide. The thickness and refractive indexes of the layers are chosen such that an optical mode confined in the sensing layer will suffer substantially anti-resonant reflection as a consequence of the interface between the sensing layer and the second layer and the interface between the second layer and the substrate. Alternatively, the waveguide may comprise a low index sensing medium held between a superstrate and a substrate each of which has a refractive index higher than that of the medium. The waveguide may be capable of supporting two modes, such that one of the modes may be used as a reference during measurement of optical properties of a medium. The waveguide may be capable of supporting a leaky waveguide mode, the presence of the leaky waveguide mode being indicated by a peak of light returned from the waveguide.

9 Claims, 27 Drawing Sheets

OTHER PUBLICATIONS

Kate A. Remley and Andreas Weisshaar, "Design and analysis of a silicon–based antiresonant reflecting optical waveguide chemical sensor", *Optics Letters*, 21(16) (1996), pp. 1241–1243.

S. Asakawa, Y. Kokubun, M. Ohyama and T. Baba, "Three–Dimensional Optical Interconnects by Stacked Arrow Waveguides", *Electronics Letters*, 29(16) (1993), pp. 1485–1486.

U. Trutschel, M. Mann, F. Lederer and C. Wachter, "Non-linear switching in coupled antiresonant reflecting optical waveguides", *Appl. Phys. Lett.*, 59(16) (1991), pp. 1940–1942.

M. Mann, U. Trutschel, C. Wachter, L. Leine and F. Lederer, "Directional coupler based on an antiresonant reflecting optical waveguide", *Optics Letters*, 16(11) (1991), pp. 805–807.

Nicholas Goddard, Dennis Pollard–Knight and Colin H. Maule, "Real–time Biomolecular Interaction Analysis Using the Resonant Mirror Sensor", *Analyst*, 119 (1994), pp. 583–588.

Thomas Delonge, Henning Fouckhardt, "Integrated optical detection cell based on Bragg reflecting waveguides", *Journal of Chromatography A*, 716 (1995), pp. 135–139.

M.A. Duguay, Y. Kokubun, T. Koch and Loren Pfeiffer, "Antiresonant reflecting optical wavelengths in SiO2–Si multilayer structures", *Appl. Phys. Lett.* 49(1) (1986), pp. 13–15.

David Fortune, "Binding and Kinetics—New Dimensions in Optical Biosensor Analysis", *Biosensors & Bioelectronics*, 8(7/8) (1993), pp. xxxii–xxxiv.

* cited by examiner

WAVEGUIDE STRUCTURES

TECHNICAL FIELD OF THE INVENTION

This invention relates to waveguide structures, and particularly though not exclusively to waveguide structures suitable for use as optical sensors.

BACKGROUND OF THE INVENTION

Sensors which are capable of monitoring biological interactions in real time and with high sensitivity are of considerable importance in life science research. Several sensors exist which monitor changes in the refractive index (or other parameters) of a biological sample, caused by molecular interactions. In a typical sensor an evanescent wave associated with an optical mode existing in a high refractive index dielectric layer of a waveguide extends into a biological sample, which is held in a gel. A change of the refractive index of the sample will modify an optical property of the waveguide mode, and detection of this change will provide dynamic information relating to interactions occurring within the biological sample.

Known optical evanescent sensors include those based on surface plasmon resonance and those based on dielectric waveguiding techniques (see for example Welford, K (1991) Surface plasmon-polaritons and their uses—*Optical and Quantum Electronics*, 23, 1–27; Smith, A. M. (1987) Optical waveguide immunosensors, *Proc. SPIE* 798 *Fibre Optic Sensors II*, 206–213); R. H. Ritchie, Phys. Rev. 106, 874 (1957).

Sensors which use surface plasmon resonance comprise a thin metal layer (typically a few tens or hundreds of Angstroms thick) deposited onto a dielectric prism or grating, and a sensing layer (or a fluid) whose optical properties are of interest provided at an opposite surface of the metal layer. Measurements are made by directing light via the prism or grating onto that side of the metal layer which is not in contact with the sensing layer, and detecting light which is reflected from the same side of the metal layer. A surface plasmon resonance excited by the incident light will result in the absorption of that incident light, and a consequent dip in the reflected light intensity. The condition for exciting a resonance (i.e. the angle of incident light which will excite a resonance) is sensitive to changes in the optical properties of the sensing layer. The optical properties of the sensing layer may be monitored by detecting changes in the angle of incidence which excites a resonance The resolution, and hence the sensitivity, of sensors which utilise surface plasmon resonance is limited by the resonance width (i.e. the range of angles of incident light which will excite resonance). This width is determined ultimately by the amount of absorption of incident light into the metal layer. Absorption is considerable at wavelengths commonly used for biological measurements, and the maximum resolution of surface plasmon sensors is correspondingly restricted.

The angle of incident light which excites a surface plasmon resonance will alter if the wavelength of the incident light is changed. Variations in the wavelength of incident light will thus introduce an error into measurements. This is a further limitation of surface plasmon resonance sensors, since wavelength-stabilised sources of incident light are needed to allow accurate measurement.

A waveguide structure, based upon the surface plasmon resonance structure and known as a leaky mode waveguide, is described by R. P. Podgorsek, H. Frarke and J. Woods (1998) Monitoring of the Diffusion of Vapour Molecules in Polymer Films using SP-Leaky-Mode Spectroscopy, *Sensors and Actuators B-Chemical*, Vol.51, No.1–3, pp.146–151. The waveguide comprises a substrate, a thin metal layer disposed on top of the substrate, and a sensing layer whose optical properties are of interest disposed as a further layer on top of the layer of metal. The sensing layer has optical properties which change if the medium is exposed to conditions to be sensed, and may be for example dextran gel.

The leaky mode excited within the sensing layer is of a type known in the art as a bulk mode. This contrasts with the mode which is excited by surface plasmon resonance sensors, which mode is known in the art as a surface mode. Generally only one mode may be excited in surface plasmon sensors (the mode must be a TM mode), whereas the leaky mode waveguide allows the excitation of a series of modes (the modes may be any combination of TE and TM).

A leaky mode of the waveguide, i.e. a bulk mode which is centred on the sensing layer, is excited by directing light towards the layer of metal or metal alloy through the substrate over a range of incident angles. The presence of an excited leaky mode is determined by detecting the intensity of light returned from the waveguide over a range of angles. When light is coupled to a leaky mode of the waveguide this is seen as a dip in the intensity of light emitted from the waveguide. A change of an optical property of the sensing layer will modify the angle of incident light required to excite the leaky mode. The angle at which the dip of intensity is returned from the waveguide will change accordingly.

The leaky mode waveguide is advantageous compared to surface plasmon resonance because a bulk mode of the waveguide is excited rather than a surface mode. This bulk mode is centred on the sensing layer of the waveguide and is therefore considerably more sensitive to changes of the optical properties of the sensing layer than the surface mode provided by surface plasmon resonance.

A disadvantage of known leaky mode waveguides is that detection optics are required to detect a dip in the intensity of light returned from the waveguide, and to follow angular movement of that dip. The absence of light is inherently more difficult to detect than a peak of light intensity.

SUMMARY OF THE INVENTION

It is an object of the invention to provide a leaky mode waveguide which will return a peak of intensity when a leaky waveguide mode is excited.

According to a first aspect of the invention there is provided an optical sensor comprising a waveguide having a substrate, a layer of metal or metal alloy disposed on top of the substrate, and a medium disposed as a sensing layer on top of the layer of metal or metal alloy, the medium having optical properties which change if the medium is exposed to conditions to be sensed, the sensor further comprising means for directing light towards the layer of metal or metal alloy through the substrate over a range of incident angles, and detection means for detecting the intensity of light returned from the waveguide over a range of detection angles, the means for directing light being configured to direct light such that a leaky waveguide mode is excited within the sensing layer, and the means for detecting the intensity of light being arranged to detect variations with detection angle in the intensity of returned light resulting from the excitation of the leaky waveguide mode; characterised in that the waveguide is configured such that the overlap of the optical field with the layer of metal or metal alloy is less for light incident at an angle which results in excitation of a leaky waveguide mode than for light incident at an angle which does not result in excitation of a leaky waveguide mode, whereby the detected intensity peakswat a detection angle related to an incident angle which results in excitation of a leaky waveguide mode.

The invention is advantageous because it allows for the easy detection of a waveguide mode.

The term metal alloy is intended to include mixtures of metals and mixtures of two or more elements which include at least one metal. Metals or metal alloys are used because they have a sufficiently high imaginary part of refractive index that an optical field extending into the metal or metal alloy suffers significant loss. The term metal or metal alloy is therefore intended to include any material having an imaginary part of refractive index comparable to that of a metal or metal alloy.

Preferably, the substrate comprises a prism or grating for coupling light into the waveguide mode.

An optical source comprising a laser, a light emitting diode or a source capable of producing a broad spectrum of wavelengths of light may be used to provide the incident light. The use of a light emitting diode, or a broad band source, is made possible by the relative wavelength insensitivity of the waveguide mode of the invention.

The detection means is preferably a charge-coupled-device array (CCD) comprising cells of sufficiently small dimensions to allow resolution of the intensity variations resulting from the excitation of the waveguide mode.

The detection means may comprise a single photo-diode which is capable of being translated across the light returned by the waveguide. By translating the photo-diode through a series of positions, the photo-diode may be made to provide a measurement of intensity at each position, thereby giving a measurement similar to that which will be provided by the CCD array.

The thickness of the layer of medium is preferably greater than 200 nm, and most preferably greater than 300 nm. The layer of medium is required to be thicker than that typically used for surface plasmon resonance sensors, in order to support the waveguide mode which is excited within the medium.

According to a second aspect of the invention there is provided a method of optical sensing comprising providing a waveguide comprising a substrate, a layer of metal or metal alloy disposed on top of the substrate, a medium disposed as a sensing layer on top of the layer of metal or metal alloy, the medium having optical properties which change if the medium is exposed to conditions to be sensed, directing light towards the layer of metal or metal alloy through the substrate over a range of incident angles, and detecting the intensity of light returned from the waveguide over a range of angles, wherein the incident light is directed such that a waveguide mode is excited within the sensing layer, and variations in the intensity of returned light resulting from the excitation of the waveguide mode are detected; characterised in that the waveguide is configured such that the overlap of the optical field with the layer of metal or metal alloy is less for light incident at an angle which results in excitation of a leaky waveguide mode than for light incident at an angle which does not result in excitation of a leaky waveguide mode, whereby the detected intensity peaks at a detection angle related to an incident angle which results in excitation of a leaky waveguide mode.

A disadvantage of conventional waveguides used for optical sensing is that they do not provide an optical mode centred on a sensing layer. This problem is overcome by the leaky mode waveguide.

A limitation of the leaky mode waveguide is that leaky modes are sensitive to changes of the dimensions of the layers comprising the waveguide. The waveguide must therefore be made with tight fabrication tolerances.

It is an object of the present invention to provide a waveguide structure which overcomes or mitigates the above disadvantage.

According to a third aspect of the invention there is provided a waveguide structure comprising a medium disposed as a sensing layer, a second layer of material having a refractive index greater than that of the medium, and a substrate, wherein the structure defines a waveguide capable of supporting an optical mode confined in the sensing layer, the medium is adapted for performing chemical or biological reactions within the medium which will result in a change of an optical property of the sensing layer of the waveguide, and the thickness and refractive indices of the layers are chosen such that an optical mode confined in the sensing layer will suffer substantially anti-resonant reflection as a consequence of the interface between the sensing layer and the second layer and the interface between the second layer and the substrate.

The sensing layer is bounded on one side by a material whose refractive index is lower than that of the sensing layer.

The reference in the statement of invention to a mode being confined in the sensing layer of the waveguide structure is intended to mean that the mode is centred on that layer of the waveguide, and it will be appreciated that a proportion of the mode will extend beyond that layer.

The inventors have realised that anti-resonant reflecting optical waveguides (ARROW's) may be used to concentrate an optical field in a sensing region having a low refractive index. Since biochemical sample separation, antibody-antigen interactions, etc. are usually carried out in low index layer (dextran gel, a polymer or other suitable medium), ARROW waveguides allow concentration of an optical field in a region in which a chemical or biological reaction is to take place (i.e. the sensing layer of the above waveguide structure).

According to a fourth aspect of the invention there is provided a waveguide structure comprising a medium disposed as a sensing layer, a second layer of material having a refractive index greater than that of the medium, and a substrate, wherein the structure defines a waveguide capable of supporting an optical mode confined in the sensing layer, the medium is adapted for performing chemical or biological reactions within the medium which will result in a change of an optical property of the sensing layer of the waveguide, and the thickness and refractive indices of the layers are chosen such that an optical mode confined in the sensing layer will suffer substantially resonant reflection as a consequence of the interface between the sensing layer and the second layer and the interface between the second layer and the substrate.

The use of a resonant reflection to confine the optical mode, rather than an anti-resonant reflection, is advantageous because it renders the optical mode more sensitive to a change of an optical property of the sensing layer of the waveguide. Waveguides configured to provide an optical mode confined by resonant reflection are hereafter referred to as resonant optical waveguides (ROW's).

The medium adapted for performing chemical or biological reactions in the ARROW or ROW waveguides is preferably dextran gel, but may be any other suitable low-index material.

Preferably, the ARROW or ROW waveguide structure is adapted for use as part of an optical sensing apparatus.

Preferably, the optical sensing apparatus comprises the waveguide structure, an optical source, means for coupling light from the optical source into an optical mode confined in the sensing layer of the structure, and means for detecting changes in the properties of the optical mode by monitoring properties of light coupled from the waveguide structure.

Preferably, the coupling means comprises a prism which is located against or adjacent the substrate of the waveguide structure, the prism being configured to allow light to be coupled into a resonant optical mode confined in the sensing layer of the structure, when the light is incident upon the prism at a predetermined angle. A change of the refractive index of the sensing layer of the structure will modify the angle which will excite a resonant mode of the waveguide structure Preferably, the optical sensing apparatus is provided with means for scanning the light from the optical source so that it is incident at the waveguide over a range of incident angles. This may be done for example by mounting the optical source on a swinging arm. In the alternative, means may be provided to direct light from the optical source onto the waveguide from many angles simultaneously.

Preferably, the optical sensing apparatus is provided with means for providing light capable of exciting both TE and TM modes confined in the sensing layer of the waveguide structure, and means for producing interference between light coupled from the TE and TM modes, once it has been coupled out of the waveguide structure.

The optical source used to excite an ARROW waveguide mode may be a light emitting diode, or may be capable of producing a broad spectrum of wavelengths of light. The use of a light emitting diode, or a white light source, is made possible by the relative insensitivity of the ARROW mode index to variations of the wavelength of incident light. If a narrow wavelength band of incident light is required, a laser may be used as the light source. A narrow wavelength band will be required to excite a ROW waveguide mode.

The optical apparatus may include means for detecting a dip in the intensity of the light coupled from the waveguide. Should the waveguide structure cause scattering or absorption of light confined within the sensing layers a dip in the intensity of light coupled from the waveguide will indicate the presence of a waveguide mode.

The waveguide structure may be provided with a low index spacer layer located between the second layer and the substrate. The low index spacer layer is advantageous because it allows ARROW modes and resonant mirror modes to be excited in a single waveguide, thereby allowing comparison between them. The low index spacer may similarly allow the simultaneous excitation of ROW modes and resonant mirror modes.

The waveguide structure may be arranged to cause scattering or absorption by the introduction of scattering or absorbing elements in the sensing layer or the second layer of the waveguide, or by providing either of those layers with roughened surfaces. Where the waveguide structure includes a low index spacer layer. scattering or absorbing elements may be introduced into the spacer layer. The spacer layer may be provided with roughened surfaces.

The waveguide structure may be provided with a further layer spaced apart from the second layer by a layer of lower refractive index, the further layer having a refractive index greater than that of the sensing layer. The introduction of this extra layer will decrease the losses suffered by a mode confined in the first layer of the waveguide, and will decrease the range of angles of incident light which may be used to excite a resonant mode confined in the sensing layer of the waveguide structure.

The waveguide structure may be provided with a fourth layer located on an uppermost surface of the sensing layer, the fourth layer being material with a similar refractive index to the second layer, and a fifth layer of substrate located on top of the fourth layer. The sensing layer will thus effectively be bounded on both sides by ARROW or ROW structures. This structure may be referred to as a symmetric ARROW structure or symmetric ROW structure, although the corresponding layers on either side of the sensing layer are not required to be of identical thickness or to have the same refractive index. In this configuration, the sensing layer may consist of a fluid that may be allowed to flow through the waveguide structure. This configuration allows an optical mode to be confined in the fluid, and thereby allows the properties of the fluid to be monitored.

Optical sensing apparatus for use with a waveguide comprising the above symmetric waveguide structure may include means for detecting a dip in the intensity of the light coupled from the waveguide. Resonant modes of the waveguide will be manifest as dips in the intensity of light reflected from the waveguide structure or peaks in the intensity of light transmitted by the waveguide structure The optical apparatus may be configured to detect the presence of gases or chemicals suspended in the air, water or other fluid. One way in which this may be done is by forming the sensing layer of the waveguide structure from a polymer or other material whose refractive index, density or other property is sensitive (i.e. altered) by the presence of that chemical or biochemical species that is to be detected.

The optical apparatus may be arranged to monitor changes of the refractive index of the sensing layer of the waveguide structure, or alternatively the apparatus may be arranged to monitor fluorescence or absorption within the sensing layer.

According to a fifth aspect of the invention there is provided a method of optical sensing, comprising coupling light into a mode confined in the sensing layer of a waveguide structure described in accordance with the third aspect of the invention or the fourth aspect of the invention, coupling light out of the waveguide structure using a prism, and monitoring the angle at which coupling of light to the mode passes through a resonance.

The method may include coupling white light into a mode confined in the sensing layer of the waveguide structure described in accordance with the third aspect of the invention, thereby allowing the spectroscopic analysis of biological samples.

It is an object of the present invention to provide an alternative waveguide structure which supports an optical mode centre on a sensing layer.

According to a sixth aspect of the invention there is provided a waveguide comprising a sensing layer of a medium, a second layer forming a lower surface of the medium and having a refractive index greater than that of the medium, and a third layer forming an upper surface of the medium and having a refractive index greater than that of the medium, wherein the medium is adapted for performing chemical or biological reactions within the medium which will result in a change of an optical property of the sensing layer of the waveguide, and the waveguide is capable of supporting an optical mode centred on the sensing layer.

The waveguide, which will be referred to as a light condenser, is advantageous because its structure is very simple, and it is robust with respect to environmental changes (for example temperature fluctuations).

The light condenser mode is centred on the sensing layer, thereby providing sensitive measurement of changes of the optical properties of the medium comprising the sensing layer.

According to a seventh aspect of the invention there is provided a waveguide comprising a sensing layer of a medium, a second layer forming a lower surface of the medium and having a refractive index greater than that of the medium, and a third layer forming an upper surface of the medium and having a refractive index less than that of the medium, wherein the medium is adapted for performing chemical or biological reactions within the medium which will result in a change of an optical property of the sensing layer of the waveguide, and the waveguide is capable of supporting an optical mode centred on the sensing layer The waveguide according to the seventh aspect of the invention provides a light condenser reflection at the interface between the layer of medium and the second layer, and conventional total internal reflection at the interface between the layer of medium and the third layer.

A known construction of optical sensor, referred to as a resonant mirror biosensor, attempts to combine the sensitivity of waveguiding devices with the simple construction and use of surface plasmon resonance devices (see Cush, R. et al (1993) The resonant mirror, *Biosensors & Bioelectronics,* 8, 347–353). The resonant mirror biosensor is similar in construction to a surface plasmon resonance device. A sensing layer, i.e. the material whose optical properties are to be monitored, is placed in contact with a high refractive index layer. The refractive index and thickness (typically about 100 nm) of the high index layer are selected in such a way that the sensitivity of the sensor is maximised. This high index layer is separated from a prism by a layer of lower refractive index material, called the spacer layer (e.g. silica). The refractive index and thickness (typically about 0.5 microns) of the lower index layer are selected such that the sensitivity of the sensor is maximised and/or the sharpness of the Resonant Mirror resonances are maximised. The sensitivity of the sensor and sharpness of the modes can be controlled by altering the refractive index or thickness of the high index layer and spacer layer. The refractive index of the prism also controls the sensitivity of the sensor and sharpness of the modes. The refractive index of the prism must be higher than the mode index of the Resonant Mirror modes.

The resonant mirror differs from conventional waveguide sensors in that the mode excited in the waveguide sensor is leaky in nature. This feature, which may also be seen in surface plasmon resonance waveguides, allows light to be coupled into and out of the resonant mirror via the prism.

Efficient coupling of light to the high index dielectric layer occurs only for certain angles of incident light where phase matching between an incident beam and resonant modes of the high index dielectric layer is achieved. At a resonant point, light couples into the high index dielectric layer and propagates some distance along the sensing interface before coupling back into the prism. An evanescent wave associated with the resonant modes of the high index dielectric layer will extend into the sensing layer. Changes of optical properties of the sensing layer will alter the properties of the resonant modes of the high index dielectric layer. Generally, the thickness of the high index dielectric layer is made very low, in order to maximise the proportion of the optical mode in the evanescent field interacting with the sensing layer, and so maximise the sensitivity of the device. The thin waveguiding layer generally provides a single waveguide mode (one TE mode and/or one TM mode).

Leaky resonant mirror modes in the resonant mirror biosensor may exist for both TE and TM polarisations, and are seen as fine structure in the reflected light once it has passed through an output analyser. The angles of incidence which excite modes of the high-index layer are sensitive to changes in the sensing layer, and so changes caused by assay reactions in the sensing layer may be monitored by measuring shifts in the excitation angle.

A limitation of resonant mirror waveguides is that a variation in the wavelength of light incident at a waveguide will alter the angle of incidence required to excite resonant modes of that waveguide. The effect of a change of incident wavelength cannot be separated from the effect of a refractive index change in the sensing region, and the sensitivity of an optical sensor comprising the resonant mirror is thus limited by the extent to which variations of the wavelength of incident light can be suppressed. Lasers are used to provide the narrow wavelength band of night required for resonant mirror optical sensors. Unfortunately, lasers are susceptible to an effect known as 'mode hopping' wherein the laser wavelength jumps between different values which satisfy the resonance, criteria of the laser structure. The wavelength produced by a laser will also vary with temperature due to variation of the dimensions of that laser. Known resonant mirror optical sensors attempts to minimise the wavelength variations in the output of a laser by providing a wavelength stabilisation mechanism. However, this mechanism is both complex and expensive.

Optical sensors comprising other optical waveguides structures may also be susceptible to wavelength changes.

It is an object of the present invention to provide a waveguide structure which overcomes or mitigates the above disadvantage.

According to an eighth aspect of the invention there is provided an optical sensor comprising a waveguide defined by a plurality of layers including a sensing layer comprising a sensing medium adapted for performing chemical or biological reactions which will result in a change of an optical property of the sensing layer, the layers being capable of supporting at least one optical mode, wherein at least a first component of a supported mode extends into the sensing layer to a substantial extent such that the first component is affected by changes in optical properties of the sensing layer, and at least a second component of a supported mode does not extend into the sensing layer to a substantial extent such that the second component is not substantially affected by changes in optical properties of the sensing layer, the sensor further comprising means for detecting variations in signals representative of the first and second components, and means for comparing the detected signals to identify variations which substantially affect only the first component.

The optical sensor is advantageous because the second component will be substantially unaffected by the optical properties of the layer of sensing medium, and may be used as a reference component. The first component will be affected substantially by the optical properties of the sensing layer, and may be used to measure said optical properties. An unwanted experimental variation, for example a change of wavelength of light coupled to the waveguide, since it will affect both components equally, may be removed from a measurement of the optical properties of the medium by comparison of the measurement and reference components.

Suitably, the layers are capable of supporting two modes a first of which is the first component and a second of which is the second component.

Preferably, the two modes are centred on different layers of the waveguide.

The two modes may be resonant mirror modes. Alternatively, the two modes may be anti-resonant reflecting optical waveguide (ARROW) modes, resonant optical waveguide (ROW) modes or light condenser modes. Other different forms of modes may be supported.

The optical sensor is advantageous for measurements utilising modes other than resonant mirror modes for the same reasons given above in relation to resonant mirror modes.

An optical sensor, according to the invention, which is designed to support resonant mirror modes may have a sensing layer of semi-infinite thickness, or may have a sensing layer of finite thickness. In contrast to this, an optical sensor which is designed to support ARROW modes or ROW modes must have a sensing layer of finite thickness, and cannot have a semi-infinite sensing layer.

The layers may be capable of supporting a single mode, a first portion of the single mode defining the first component which extends into the sensing layer, and a second portion of the single mode defining the second component which does not extend into the sensing layer.

According to a ninth aspect of the invention there is provided a method of optical sensing comprising exciting at least one optical mode in a waveguide structure defined by a plurality of layers including a sensing layer comprising a sensing medium adapted for performing chemical or biological reactions which will result in a change of an optical property of the sensing layer, wherein at least a first component of a supported mode is excited so as to extend into the sensing layer to a substantial extent such that the first component is affected by changes in optical properties of the sensing layer, and at least a second component of a supported mode is excited so as not to extend into the sensing layer to a substantial extent such that the second component is not substantially affected by changes in optical properties of the sensing layer, the method further comprising detecting variations in signals representative of the first and second components, and comparing the detected signals to identify variations which substantially affect only the first component.

Preferably, two modes are be supported by the layers, a first of which is the first component and a second of which is the second component. The two modes may be centred on different layers of the waveguide.

The two modes may be resonant mirror modes, or anti-resonant reflecting optical waveguide modes A single mode may be supported, a first portion of the single mode defining the first component which extends into the sensing layer, and a second portion of the single mode defining the second component which does not extend into the sensing layer.

DESCRIPTION OF THE DRAWINGS

Specific embodiments of different aspects of the invention will now be described by way of example only with reference to the accompanying drawings, in which.

DESCRIPTION OF PREFERRED EMBODIMENTS

Figure 1:
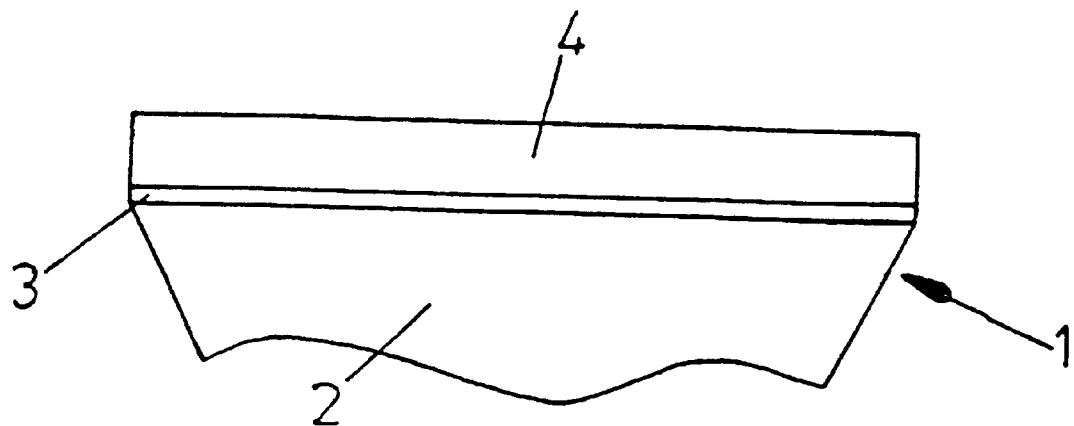
FIG. 1 is a schematic view from one side of a waveguide comprising part of an optical sensor.

A waveguide 1 comprising part of the optical sensor according to the first aspect of the invention is shown in FIG. 1. The waveguide 1 comprises a dielectric prism substrate 2, a Zirconium layer 3 deposited on an upper surface of the prism substrate 2 and a sensing layer of dextran gel 4. The Zirconium layer 3 is 20 nm thick, and the layer of dextran gel 4 in the illustrated waveguide is 800 nm thick and has a refractive index of 1.39. The prism substrate is effectively semi-infinite in thickness and has a refractive index of 1.72. An uppermost surface of the layer of dextran gel 4 is in contact with water 5 (refractive index 1.33) which is effectively semi-infinite in thickness.

The waveguide 1 is similar to waveguides which are used for surface plasmon resonance measurements. However, whereas a medium of interest used for surface plasmon resonance measurement may be semi-infinite (e.g. water), the optical sensor according to the invention requires that the medium of interest be disposed as a layer, as for example the layer of dextran gel 4 in FIG. 1.

When light is incident on the waveguide 1 at a specific angle a leaky mode will be excited. The mode is excited by light at a wavelength of 619.9 nm, which is incident at a particular angle on the prism substrate 2 of the waveguide, such that it couples through the Zirconium layer 3 and into a dextran gel layer 4. The mode is centred on the dextran gel layer 4, although a significant proportion of the amplitude extends beyond that layer and into the semi-infinite layer of water 5. The mode may be described as leaky, in the sense that a proportion of the light propagating in the mode will couple back into the prism 2. It is this leaky property which allows excitation of the mode through the prism substrate 2. The mode will hereafter be referred to as a leaky waveguide mode.

Figure 2:
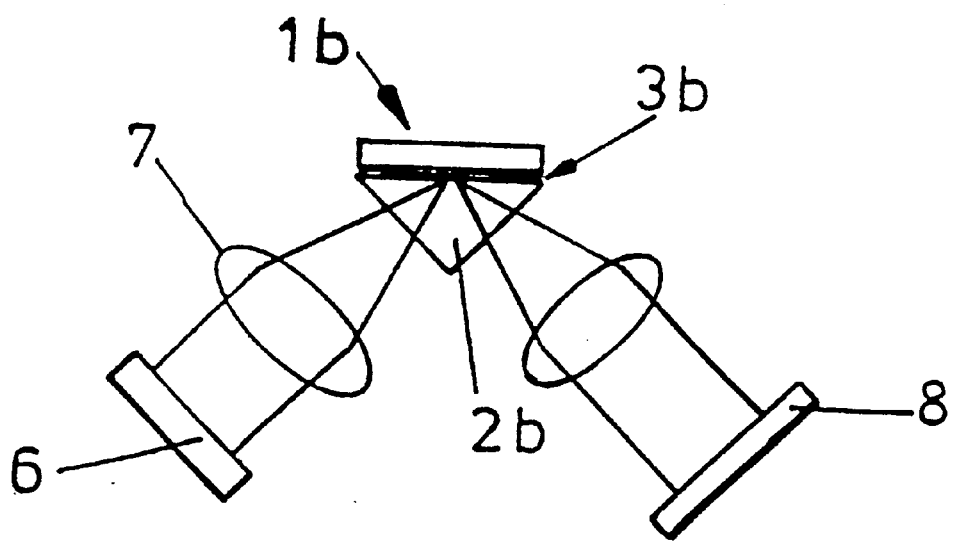
FIG. 2 is a schematic illustration of an optical sensor.

An optical sensor according to the invention is shown in FIG. 2. The sensor is similar to existing apparatus which is used to perform surface plasmon resonance measurements. The apparatus according to the invention comprises a light source 6, a lens 7 which directs a fan-shaped beam of light through a prism substrate 2 which forms part of a waveguide 1 (the waveguide corresponds to the waveguide shown in FIG. 1). Because the light is directed towards the waveguide 1 as a fan, light is incident at the waveguide 1 from a range of different angles. The prism substrate 2 is chosen to have a refractive index such that modes of the waveguide 1 are leaky, that is the modes couple into and out of the waveguide 1 easily. Although the prism substrate 2 is shown as being triangular, it could be of any suitable shape (for example rectangular), and other forms of substrate may be used. The incident light will either be coupled to a leaky waveguide mode centred on a layer of dextran gel 4, or will be reflected from the waveguide 1 without being coupled to the leaky waveguide mode, and then coupled out of the waveguide 1. Light will be coupled from the prism 2 of the waveguide 1 in the form of a fan, and will be incident upon a detector 8. The detector 8 comprises an array of charge coupled devices (CCD's) which detect the intensity of light at different sections of the fan.

The waveguide 1 is dimensioned such that the field amplitude of light in the Zirconium layer 3 is less for light incident at an angle which results in excitation of a leaky waveguide mode than for light incident at an angle which does not result in excitation of a leaky waveguide mode, and the intensity of light incident at the detector 8 therefore peaks upon excitation of a leaky waveguide mode.

If a leaky waveguide mode is excited in the waveguide 1 for a particular angle of incident light, this will be seen as a peak in the intensity of light incident at the detector 8 at one position. The position of the peak in intensity is dependent upon the refractive index of the prism 2 and on the optical properties of the layer of dextran gel 4. A chemical or biochemical reaction which modifies the optical properties of the dextran gel 4 may be monitored in real time by detecting movement of the peak.

The CCD array of the optical sensor may be replaced by a single photo-diode (not shown) mounted so as to be capable of translation in a direction perpendicular to the direction of the light reflected from the waveguide 1. In use the photo-diode would be positioned at the location of a peak in intensity, and would be translated to follow the peak of intensity during an experiment, thereby allowing measurement of the degree of movement of that peak in intensity.

It will be appreciated that the combination of the tight source 6 and lens 7 of FIG. 2 may be replaced by a light source of much smaller area, mounted on a swinging arm. The arm would be swung through a required range of angles to produce illumination at the waveguide similar to the fan of light shown in FIG. 2. The lens 7 would not be required by the swinging arm arrangement.

Figure 3:
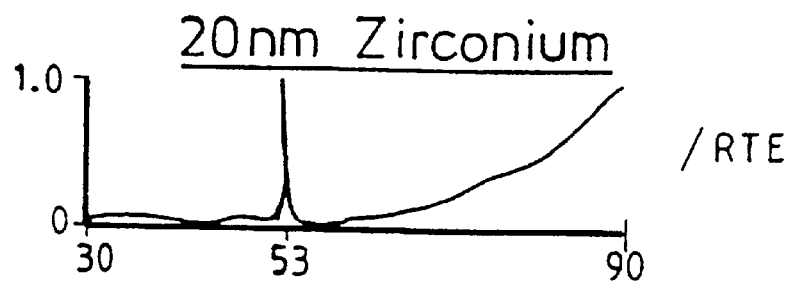
FIG. 3 is a graph of reflected intensity against incident angle which has been calculated for the waveguide illustrated in FIG. 1

FIG. 3 shows a graph of reflected intensity against incident angle, which has been calculated for the waveguide illustrated in FIG. 1 to illustrate the operation of the optical sensor according to the invention. A sharp peak in intensity is seen at approximately 53 degrees, which corresponds to a leaky TE waveguide mode.

Other examples of leaky waveguide structures which provide a peak of intensity for 619.9 nm light at resonance comprise a semi-infinite substrate (refractive index 1.72), one of the following metals or metal alloys:

| Metal/Metal Alloy | Thickness |
|---|---|
| Chromium | 3 nm |
| Manganese | 5 nm |
| Molybdenum | 4 nm |
| Nickel | 5 nm |
| Niobium | 5 nm |
| Platinum | 4 nm |
| Ruthenium | 3 nm |
| Tantalum | 9 nm |
| Tellurium | 3 nm |
| Titanium | 7 nm |
| Tungsten | 5 nm |
| Vanadium | 7 nm |
| Zirconium | 20 nm | an 800 nm thick layer of dextran gel (refractive index 1.39), and a semi-infinite layer of water (refractive index 1.33).

Figure 4:
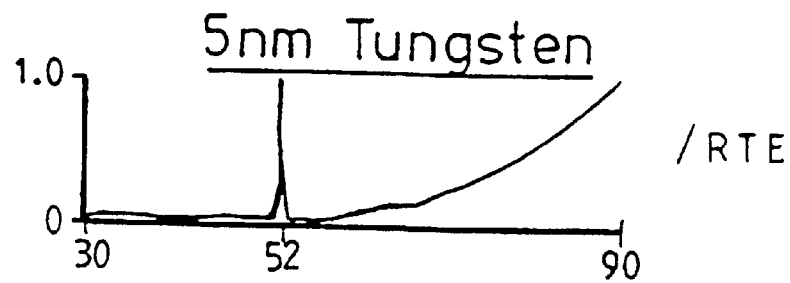
FIG. 4 is a graph of reflected intensity against incident angle which has been calculated for an alternative waveguide.

FIG. 4 shows a graph of reflected intensity against incident angle, which has been calculated for a leaky waveguide structure having a 5 nm thick layer of Tungsten (with other layers and dimensions as described above). A sharp peak in intensity is seen at approximately 53 degrees, which corresponds to a leaky TE waveguide mode.

Figure 5:
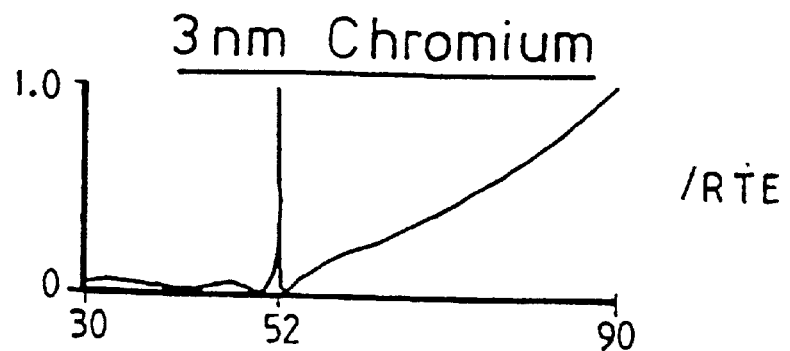
FIG. 5 is two graphs of reflected intensity against incident angle which have been calculated for two alternative waveguides.
Figure 5:
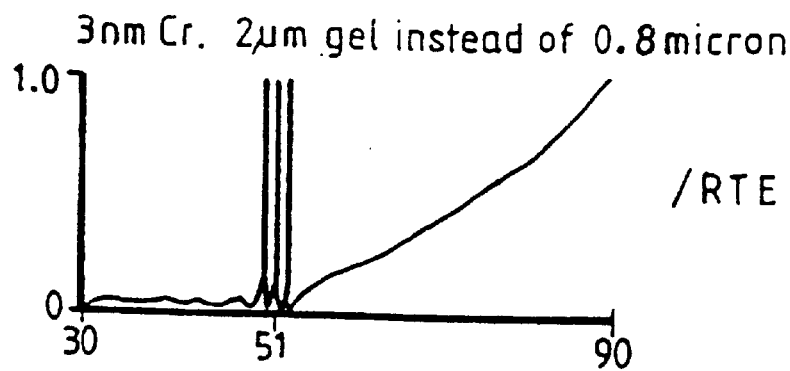

FIG. 5 shows a graph of reflected intensity against incident angle, which has been calculated for a leaky waveguide structure having a 3 nm thick layer of Chromium (with other layers and dimensions as described above for FIG. 5a, and with a 2000 nm thick layer of dextran gel for in FIG. 5b). A sharp peak in intensity is seen in FIG. 5a at approximately 53 degrees, which corresponds to a leaky TE waveguide mode. Three sharp peaks in intensity are seen in FIG. 5b between 50 and 54 degrees, which correspond to three leaky TE waveguide modes.

The invention is advantageous because the precise detection of the location of a peak of intensity is more easily achieved than the detection of the location of a dip in intensity (prior art leaky mode waveguides provide only dips in intensity).

The inventors have realised that the generation of a peak of output rather than a dip of output from a leaky mode waveguide is determined by the field amplitude of light in the metal layer of the waveguide. Light having a large field amplitude in the metal layer of the leaky mode waveguide will suffer significant loss, as energy is deposited as heat in the metal. A leaky mode waveguide may be configured to provide a peak of output by arranging the waveguide such that the amplitude of the mode in the metal layer is low when the leaky mode is excited.

FIGS. 6 to 17 show results from a computer model indicating how a leaky mode waveguide may be configured to provide a peak of output. A conventional leaky mode waveguide having the following dimensions:

| Region | Refractive index | Thickness | Label |
| --- | --- | --- | --- |
| Substrate | 1.72 | Semi-infinite | 9 |
| Metal (Gold) | 0.13–3.16i | 0.05 microns | 10 |
| Sensing layer | 1.38 | 2.0 microns | 11 |
| Superstrate | 1.333 | Semi-infinite | 12 | is excited with incident light at 619.9 nm. The angle of incidence of the light is measured relative to a normal from the plane of the metal layer 10.

Figure 6:
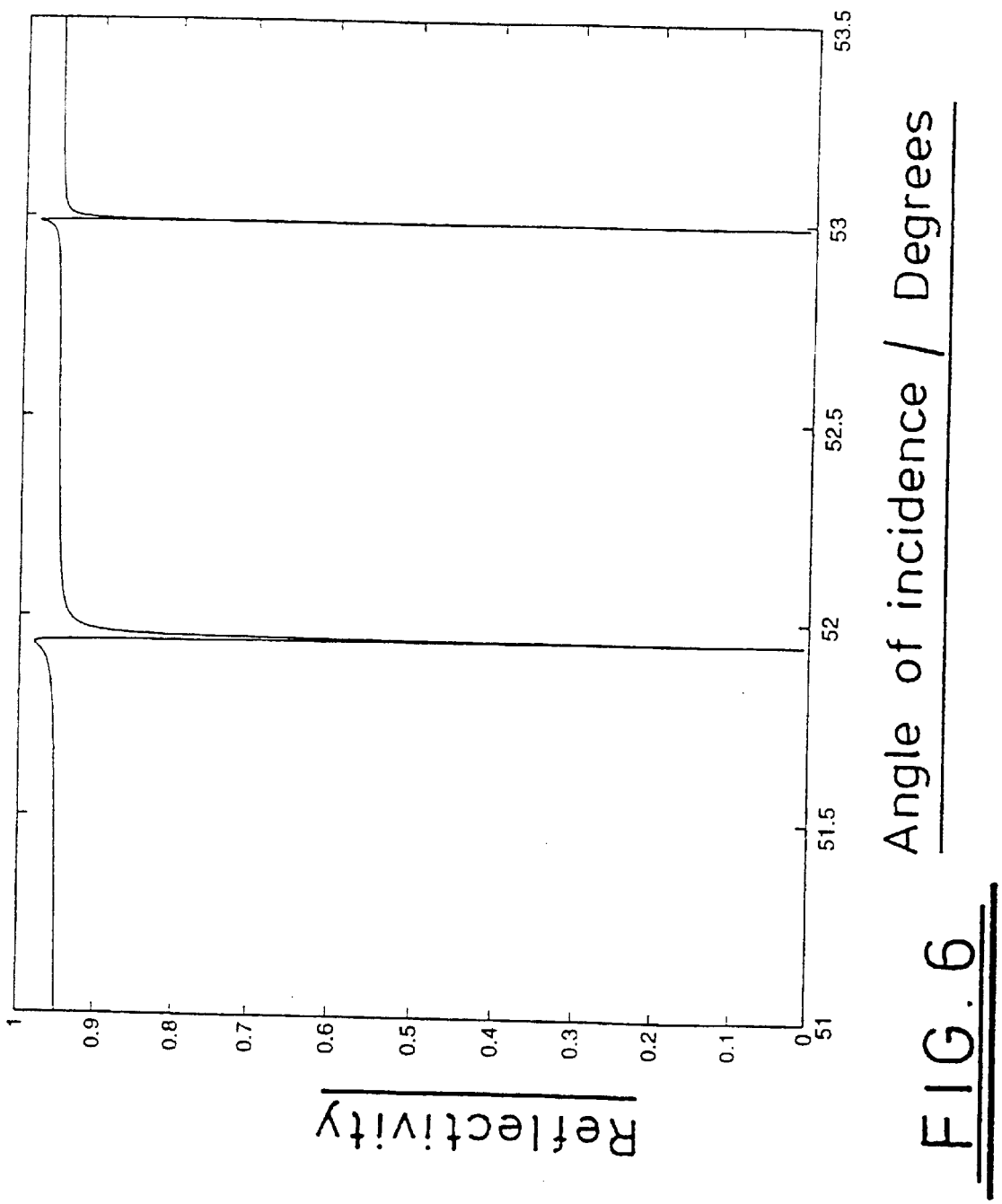
FIG. 6 is a graph of reflected intensity against incident angle which has been calculated for an alternative waveguide.

A plot of reflectivity against angle of incidence for the waveguide described in the table is shown in FIG. 6. The dips in the plot are due to leaky modes being excited in the sensing layer 11. In this case, (as in prior art leaky mode waveguides) when the modes are excited, the overlap between the mode and the metal layer 10 increases. This leads to optical power loss, and this manifests itself as dips in the reflectivity.

Figure 7:
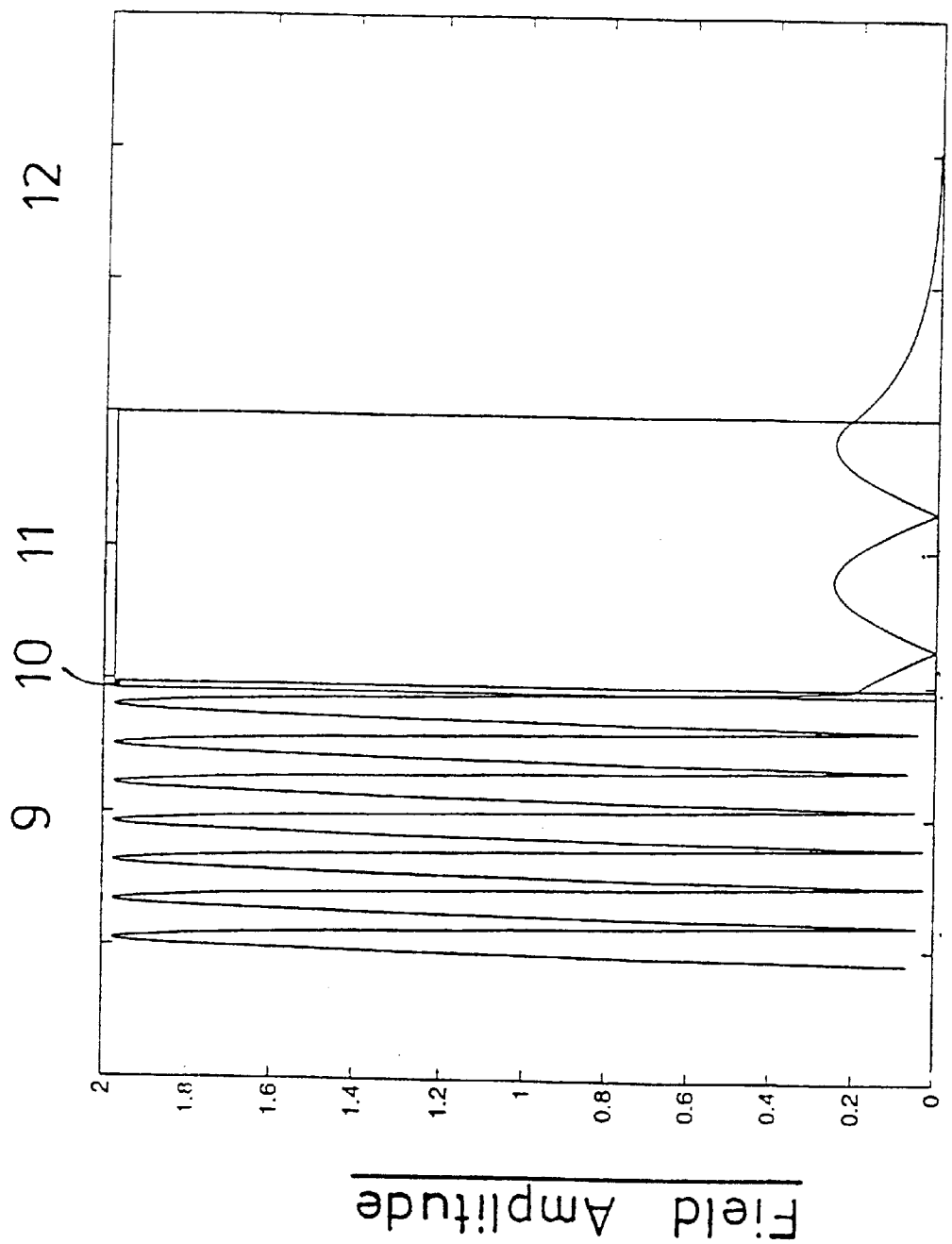
FIGS. 7 to 11 are graphs of field amplitude which have been calculated for the waveguide of FIG. 6.

FIGS. 7 to 11 illustrate the optical field amplitude in the waveguide described in the table, for a variety of angles of incident light. FIG. 7 shows the amplitude of the optical field in the waveguide when the angle of incidence is 51.5 degrees. The amplitude is normalised, with the average amplitude of incident light being set at 1. Light in the substrate 9 of the waveguide is simply laser light at 619.9 nm and oscillates between 0 and 2. The normalised amplitude of light in the gold layer 10 is approximately 0.3. The normalised amplitude of light in the sensing layer 11 is approximately 0.3, and decays gradually into the substrate 12. A leaky mode of the waveguide is not excited by the light incident at 51.5, as is indicated by the low amplitude of light in the sensing layer 11.

Figure 8:
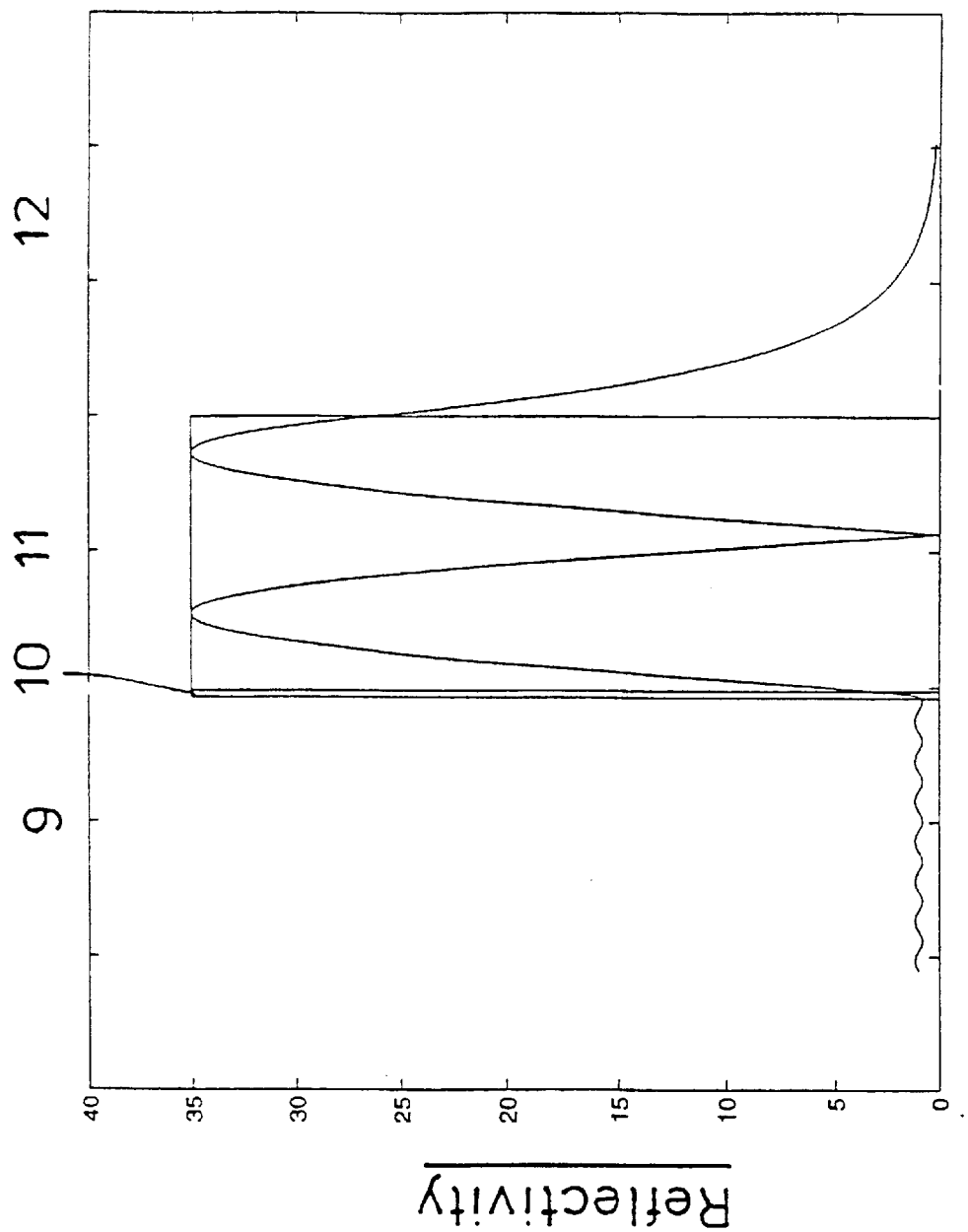

FIG. 8 shows the amplitude of the optical field at an angle of resonance of 51.94485 degrees (i.e. an angle of incident light at which a leaky mode is excited). The leaky mode is clearly shown by the fact that the optical field in the sensing layer 11 is approximately 35. The excited mode is a second order leaky mode of the waveguide. The average amplitude of the field in the metal at this angle of incidence is approximately 2. This means that more energy is being deposited as heat in the metal layer 10 at this angle of incidence than at 51.5 degrees, and the reflectivity of the waveguide is correspondingly reduced. This explains the presence of the dip of reflectivity seen at 51.94485 degrees in FIG. 6.

Figure 9:
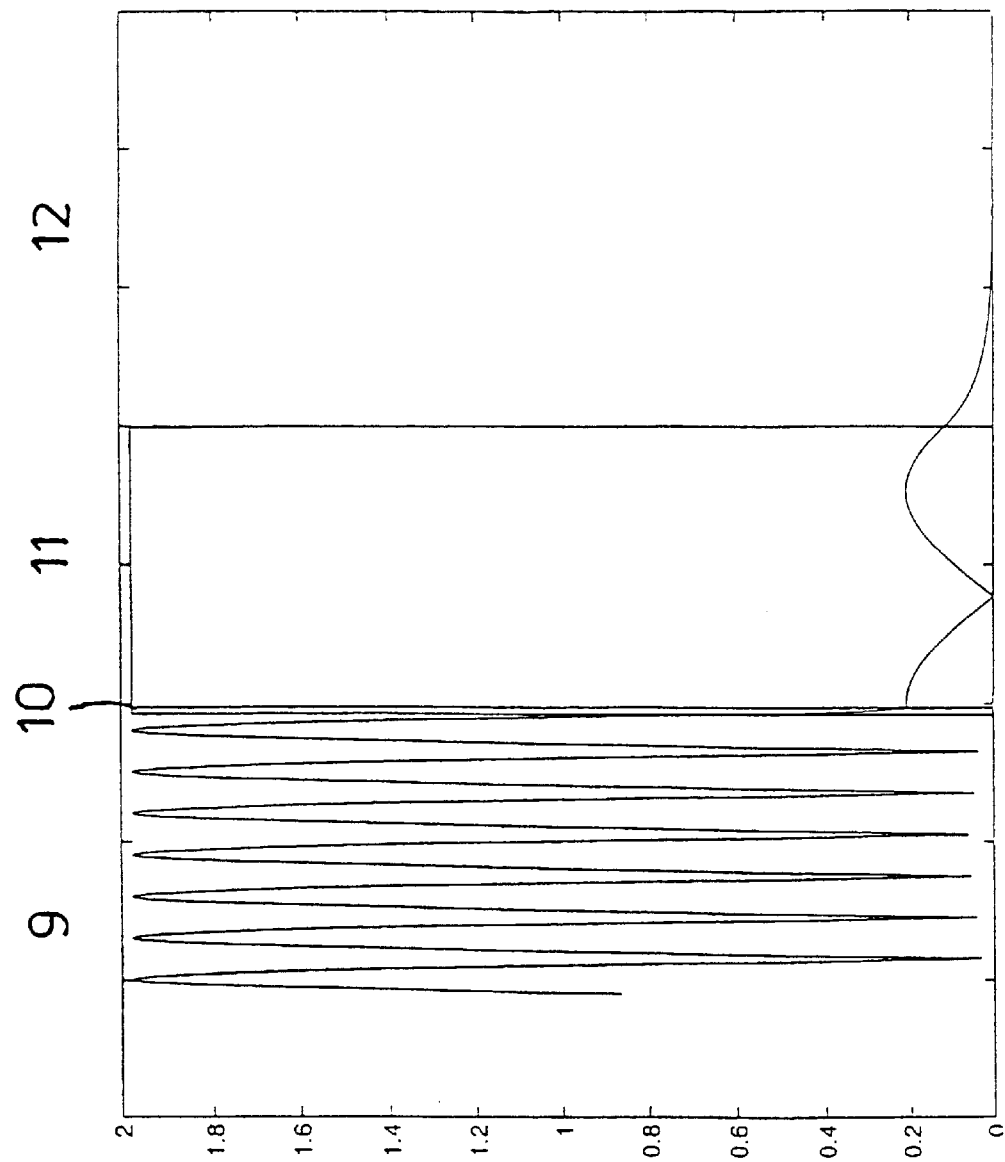
Figure 10:
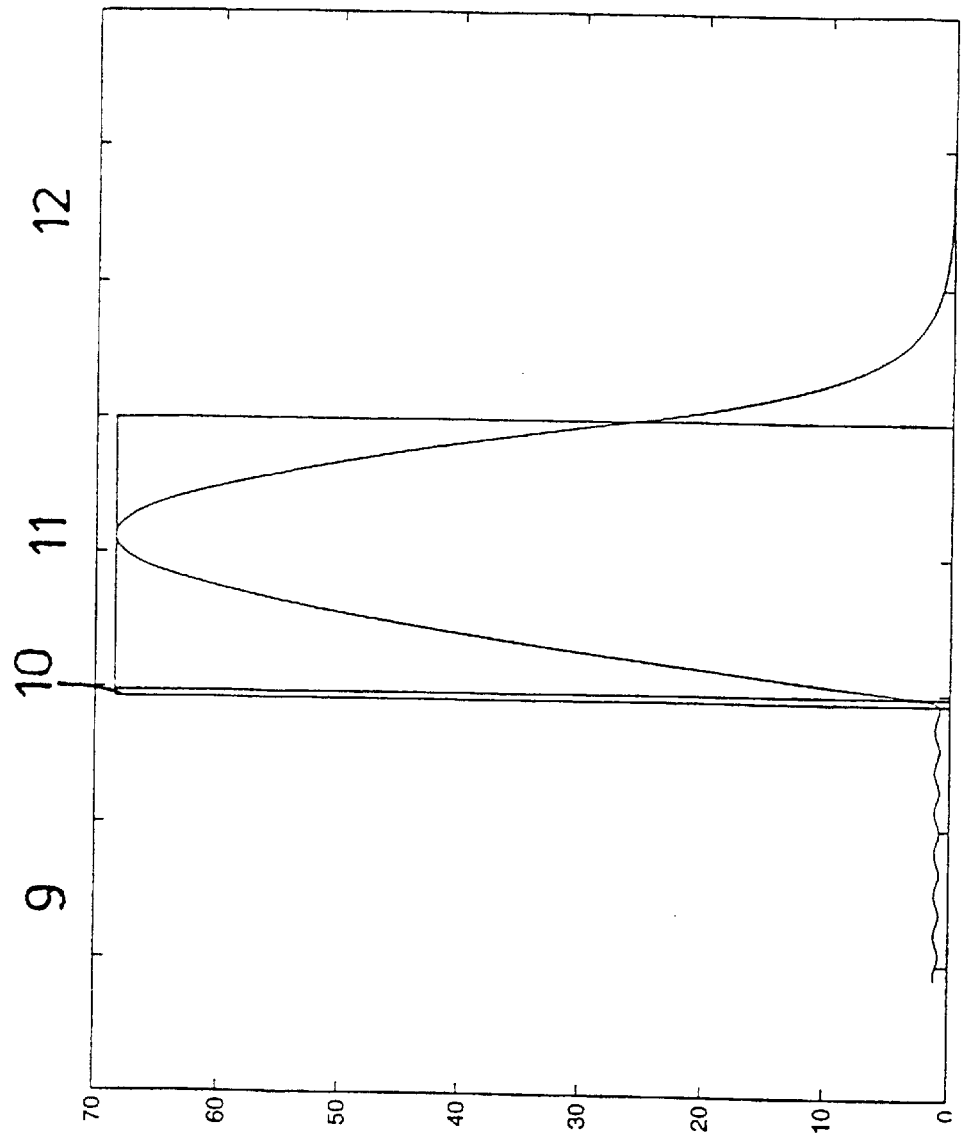
Figure 11:
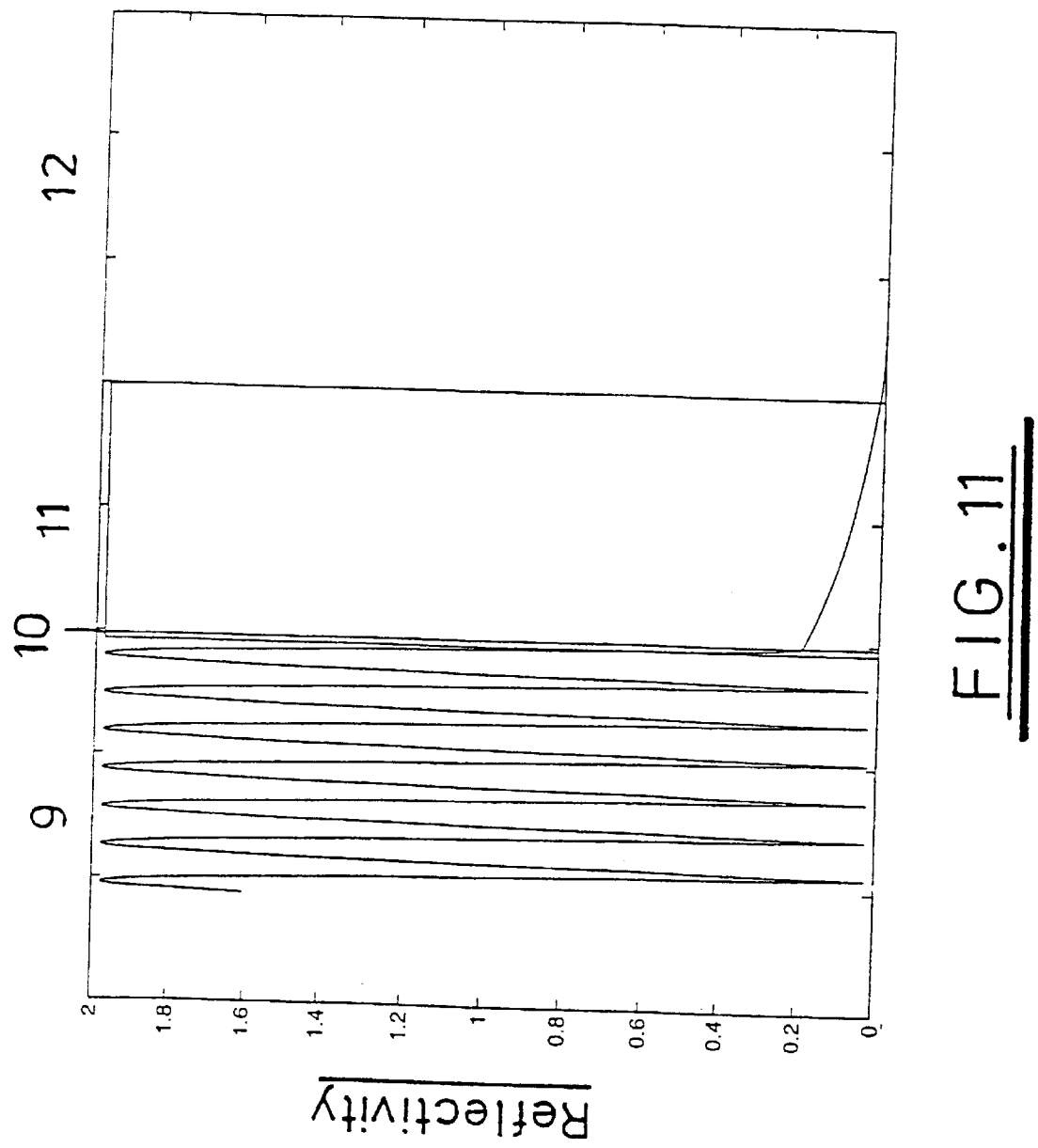

FIGS. 9 and 10 show the amplitude of the optical field in the waveguide for incident light at 52.5 degrees (no leaky mode excitation) and 53.99036 degrees (first order leaky mode excited) respectively. The average amplitude of the field in the metal layer 10 in FIG. 9 is approximately 0.3. This is a relatively low value, and so the reflectivity at this point is relatively high. In FIG. 10, the field amplitude in the metal layer 10 is approximately 1.5, so that there is a dip in reflectively at this point. FIG. 11 shows the amplitude of the optical field in the waveguide for incident light at 53.5 degrees. The amplitude of the field in the metal layer 10 is low (approximately 0.3), so that the reflectivity of the waveguide is relatively high.

As a further example of the present invention, a leaky mode waveguide was prepared having the following dimensions:

| Region | Refractive index | Thickness | Label |
| --- | --- | --- | --- |
| Substrate | 1.72 | Semi-infinite | 13 |
| Metal (Chromium) | 0.48–4.36i | 0.005 microns | 14 |
| Sensing layer | 1.38 | 2.0 microns | 15 |
| Superstrate | 1.333 | Semi-infinite | 16 | and excited with incident light at 619.9 nm. Again, the angle of incidence of the light is measured relative to a normal from the plane of the metal layer 14.

Figure 12:
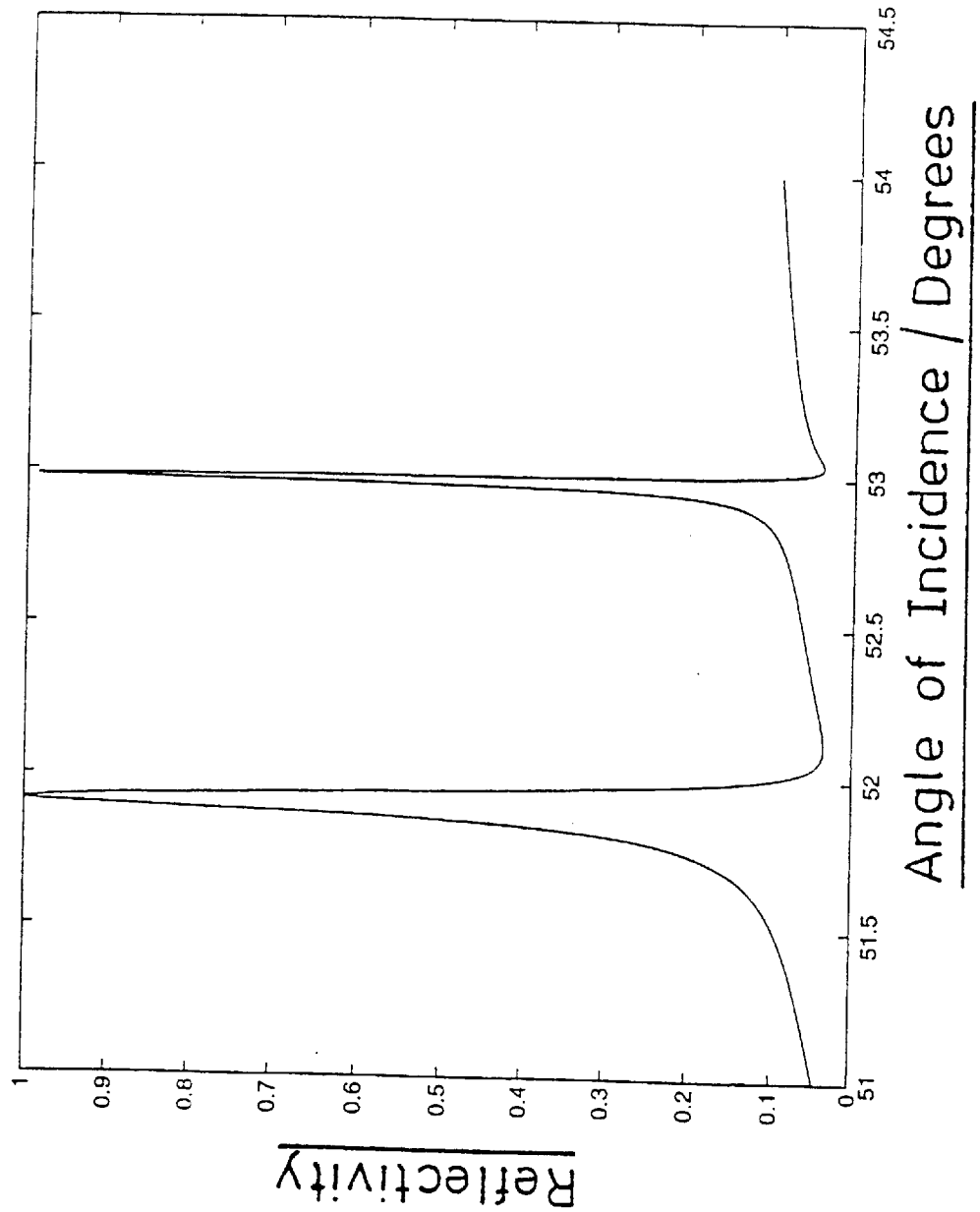
FIG. 12 is a graph of reflected intensity against incident angle which has been calculated for an alternative waveguide.
Figure 13:
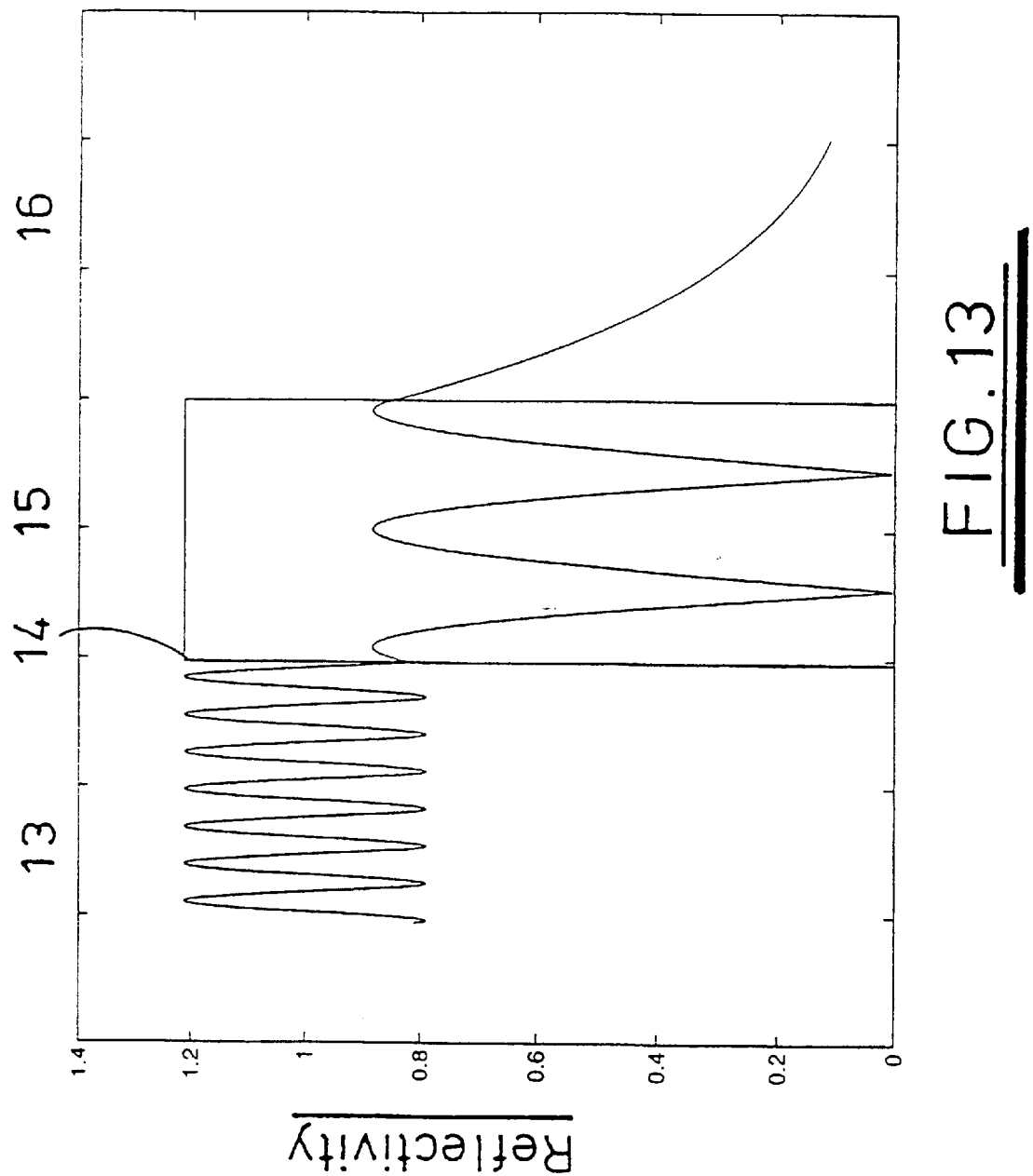
FIGS. 13 to 17 are graphs of field amplitude which have been calculated for the waveguide of FIG. 6.

A plot of reflectivity against angle of incidence for the waveguide described in the above table is shown in FIG. 12. In this case, there are peaks rather than dips in the reflectivity plot, which correspond to the presence in the waveguide of leaky modes. The reason for this can be seen from the FIGS. 13 to 17, which illustrate the amplitude of the optical field as a function of angle of incidence.

Figure 14:
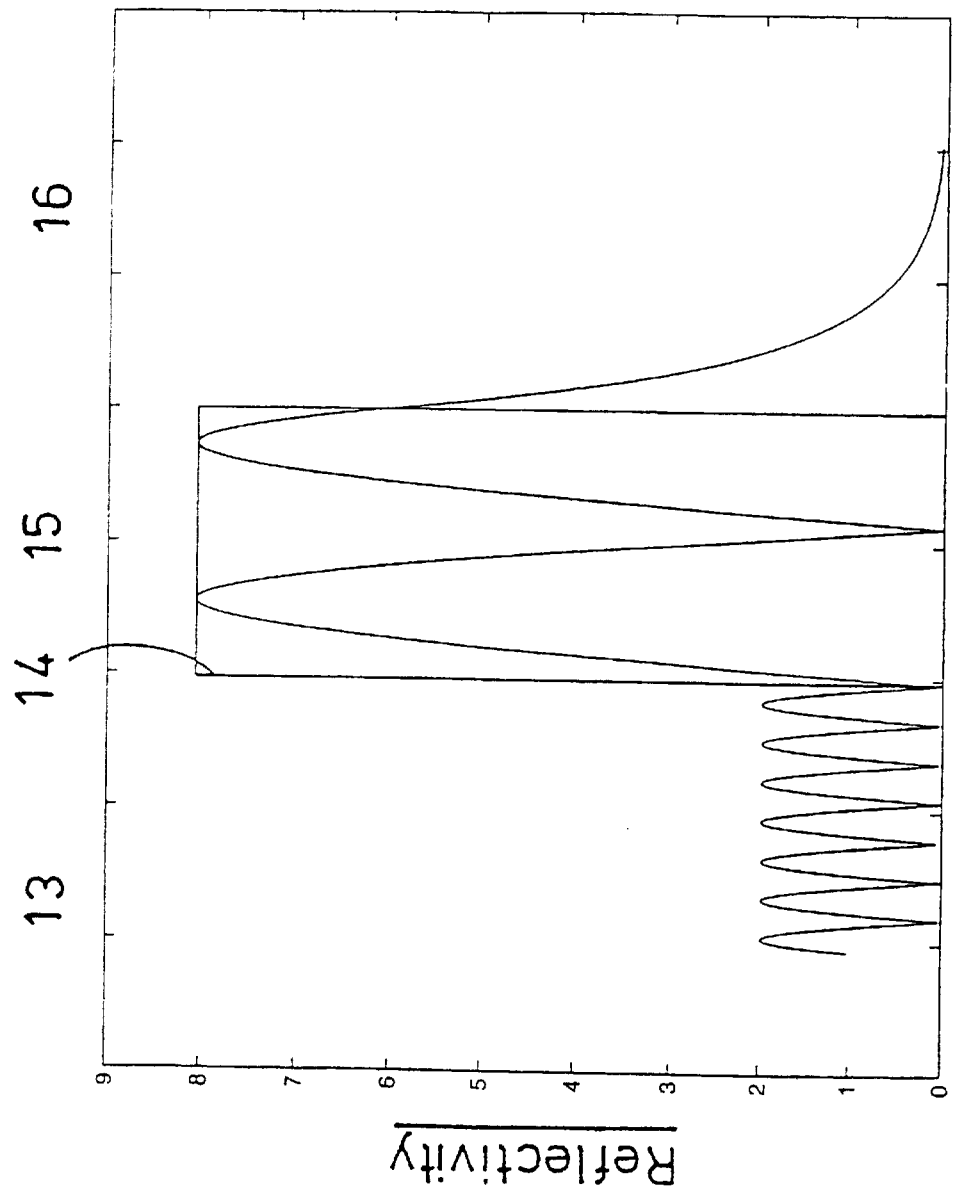
Figure 15:
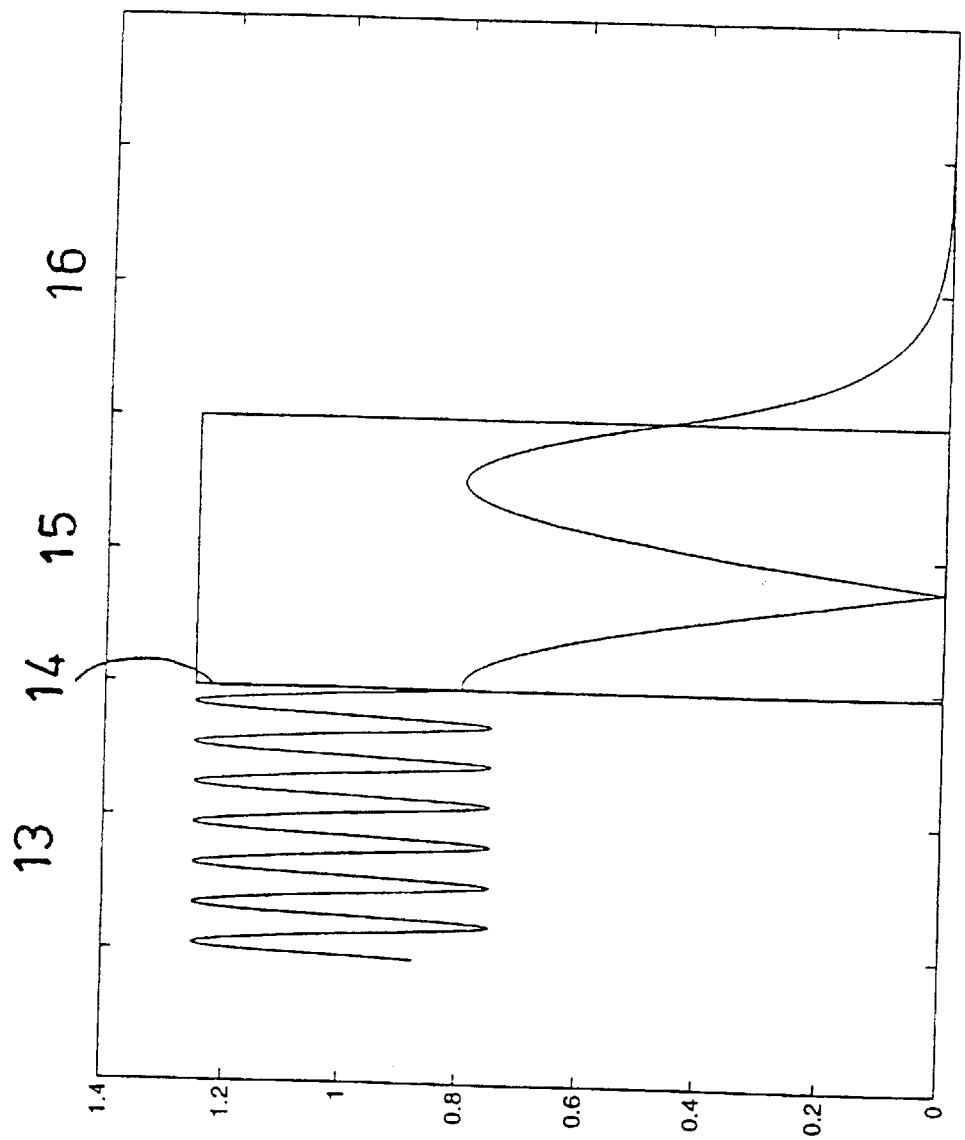
Figure 16:
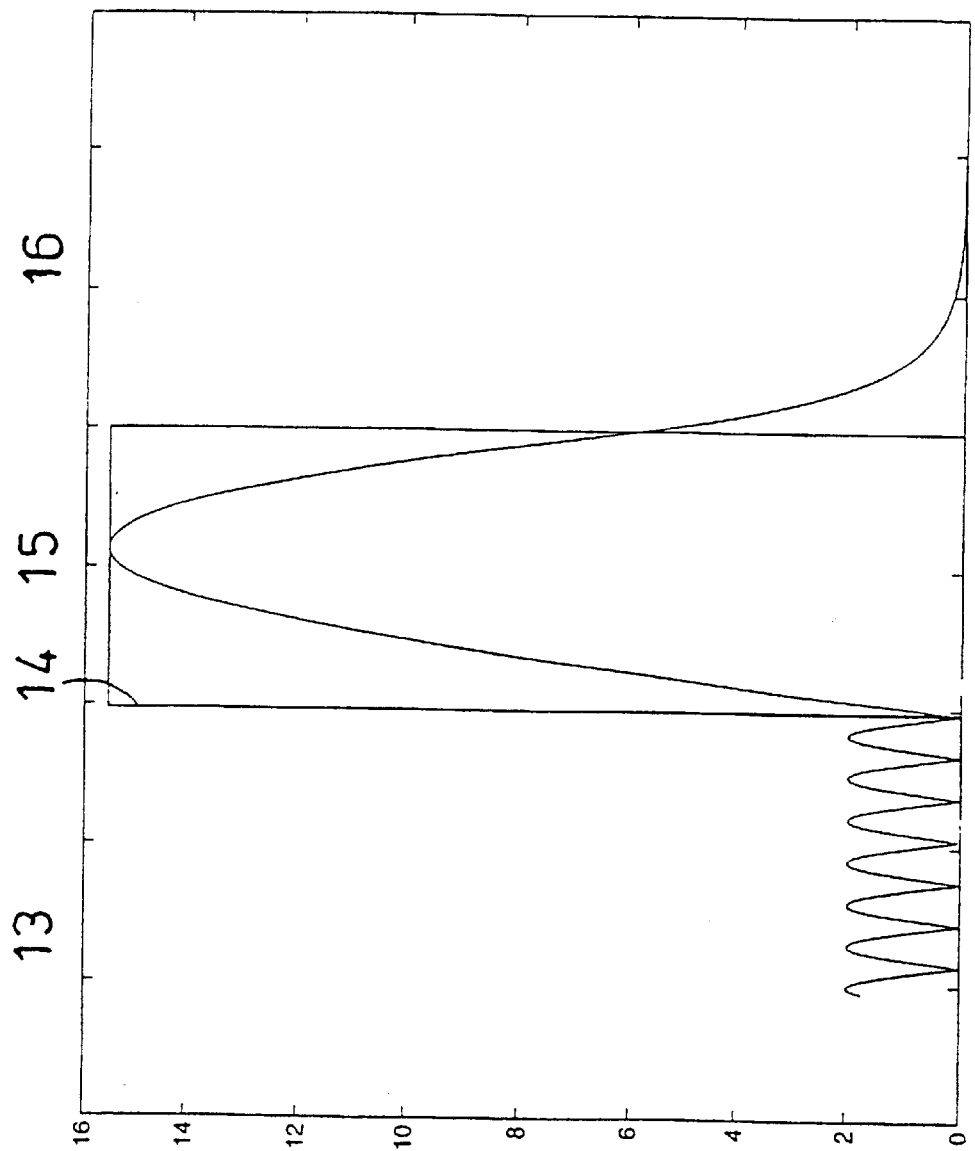
Figure 17:
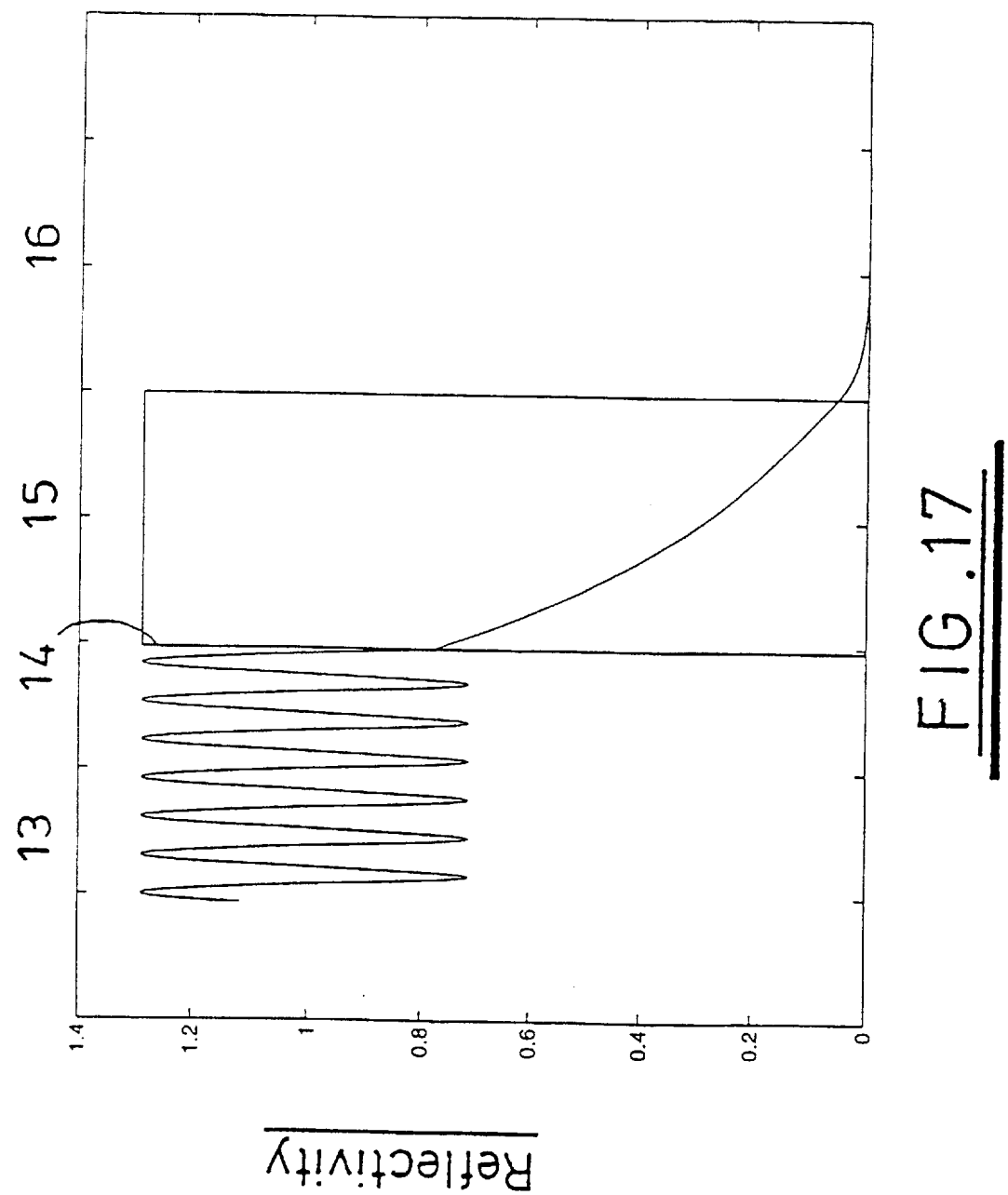

FIGS. 14 & 16 show leaky modes excited in the waveguide at 51.92151 degrees (a second order leaky mode) and 52.9841 degrees (a first order leaky mode). At these angles, the amplitude of the optical field in the metal layer 14 is almost zero. Therefore a negligible amount of energy is removed from the system and so the reflectivity of the waveguide is close to 1.0 when the leaky modes are excited. For light incident at 51.0, 52.5 and 53.5 degrees (FIGS. 13, 15 & 17) the amplitude of the optical field in the metal layer 14 is relatively high, and so the reflectivity at these points is relatively low.

The use of a leaky mode waveguide is advantageous in that a variation of the wavelength of incident light will not produce a significant variation in the angle of incidence required to excite a leaky waveguide mode. This contrasts with surface plasmon resonance, wherein a variation of the wavelength of incident light will introduce an error into an angular measurement. Sources of incident light other than lasers may be used without significant loss of resolution, for example a light emitting diode or other broad band source. The use of a light emitting diode, which produces light over a wider band of frequencies than would be produced by an equivalent laser, is made possible by the relative wavelength insensitivity of the leaky waveguide mode. Light emitting diodes and other broad band sources are advantageous because they do not suffer from 'speckling', which degrades the performance of instruments that use diode lasers. The use of a broad band light source will allow the spectroscopic analysis of biological samples—something that is difficult or impossible to do with surface plasmon resonance sensors.

Since leaky waveguide modes of TE or TM polarisation may be excited according to the invention, control of the polarisation of incident light is not necessary. Polarisation control is preferred because it allows the relative magnitudes of the TE and TM modes to be fixed. This contrasts with surface plasmon resonance waveguides, wherein only one TM mode may be excited and the incident light is polarised accordingly.

Figure 18:
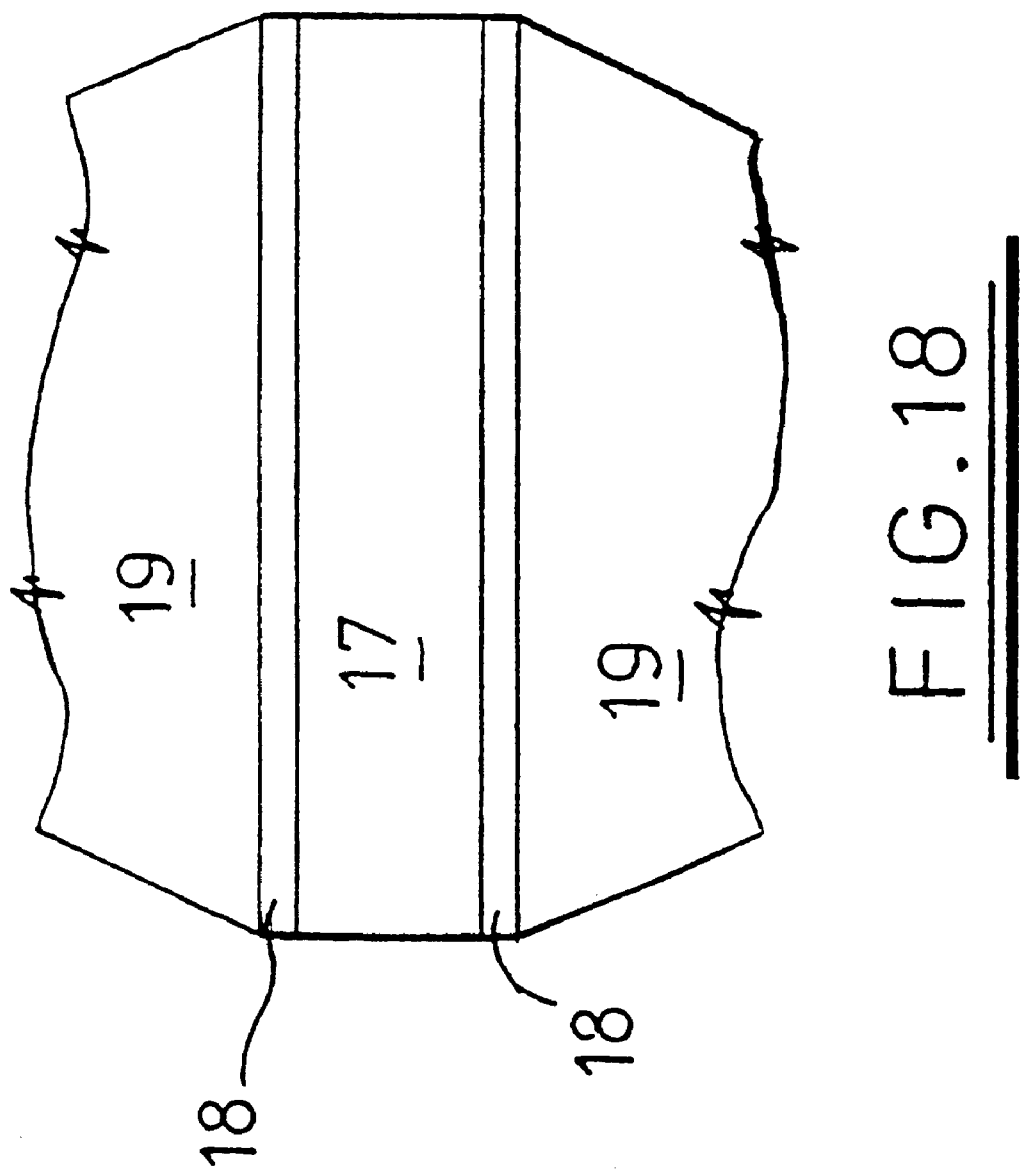
FIG. 18 is a schematic view from one side of a waveguide comprising part of an optical sensor.

An alternative form of leaky mode waveguide is illustrated in FIG. 18. The waveguide comprises a layer of dextran gel 17 bounded on either side by a metal layer 18 and a substrate 19. A mode (or modes) may be excited in the waveguide shown in FIG. 18 in the manner described above. The mode will be more tightly confined within the layer of dextran gel 17 than a mode confined in the waveguide structure shown in FIG. 1.

Waveguides of the form shown in FIG. 18 may be described as symmetric, although it is not necessary to their operation that they be strictly symmetric. A feature of symmetric waveguides is that, as well as reflection of incident light, they also provide transmission of incident light, since modes of the waveguides may be arranged to be leaky on both sides of the gel layer 17. This is not the case with waveguides of the form shown in FIG. 1, in which transmission of light is inhibited.

A construction of symmetric waveguide with a central layer consisting of fluid (rather than the dextran gel 17) may be used to detect refractive index changes in that fluid. Changes of the refractive index of the fluid are monitored using the techniques described above.

The leaky mode waveguide may be used in the measurement of fluorescence (by including a fluorescent species in the sensing layer).

Figure 19:
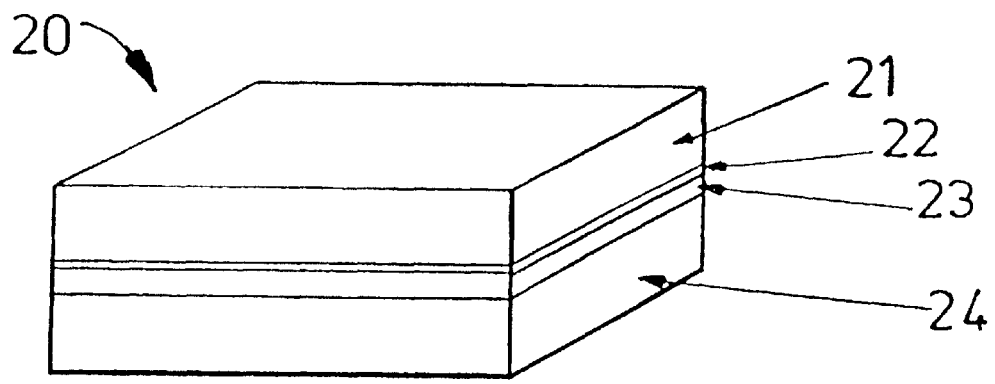
FIG. 19 is a schematic perspective view of a waveguide structures.

An alternative waveguide structure which may be used as an optical sensor is shown in FIG. 19. The waveguide is an Anti-Resonant Reflecting Optical Waveguide (ARROW). ARROW's are a class of waveguide which exhibit special propagation characteristics that make them suited to optical sensing applications.

ARROW waveguides were first developed in 1986 at AT&T Bell labs, and are described in the paper: Duguay et al, Appl. Phys. Lett., 49 (1986) 13–15. The waveguide 20 shown in FIG. 19 is an ARROW structure, and comprises a sensing layer 21 (approx. 4 $\mu$m) of low refractive index gel (or other low index substance of interest) situated on top of a thin high index layer 22 (approx. 0.1 $\mu$m), which in turn is located on top of a layer of silica 23 (approx. 0.5 $\mu$m). The entire structure is supported on a transmissive substrate 24 (for example glass). Light propagating in the sensing layer 21 of the waveguide 20 will undergo total internal reflection at an interface between an upper surface of the sensing layer 21 and the surrounding air or other low index medium, and undergo very high reflection from high index layer 22. The high index layer 22 acts as a Fabry-Perot resonator at anti-resonant wavelengths, providing a very high degree of confinement of the optical mode within the sensing layer 21.

It is within the sensing layer 21 of the waveguide 20 that molecular interactions (or any other interactions) which are to be studied occur. The waveguide 20 thus exploits an important advantage of ARROW structures, namely that they allow concentration of an optical field in a low refractive index region of interest. This feature is important since biological sample separation, antibody-antigen interactions etc. are usually carried out in low index dextran gel. The waveguide 20 allows an optical field to be concentrated in the dextran gel (i.e. sensing layer 21), whereas in most known prior art waveguides the field is localised in a high refractive index layer adjacent to the dextran gel. The enhanced overlap in the waveguide 20 between the optical field and the region to be monitored provides significantly increased sensitivity.

The waveguide 20 is easy to fabricate, and dispersion characteristics of ARROW modes are such that even a quite large variation in waveguide parameters, i.e. layer thickness or refractive index, does not significantly affect the operation of the waveguide. This is a significant advantage of the invention, since conventional known waveguides are very sensitive to variation of waveguide parameters.

Figure 20:
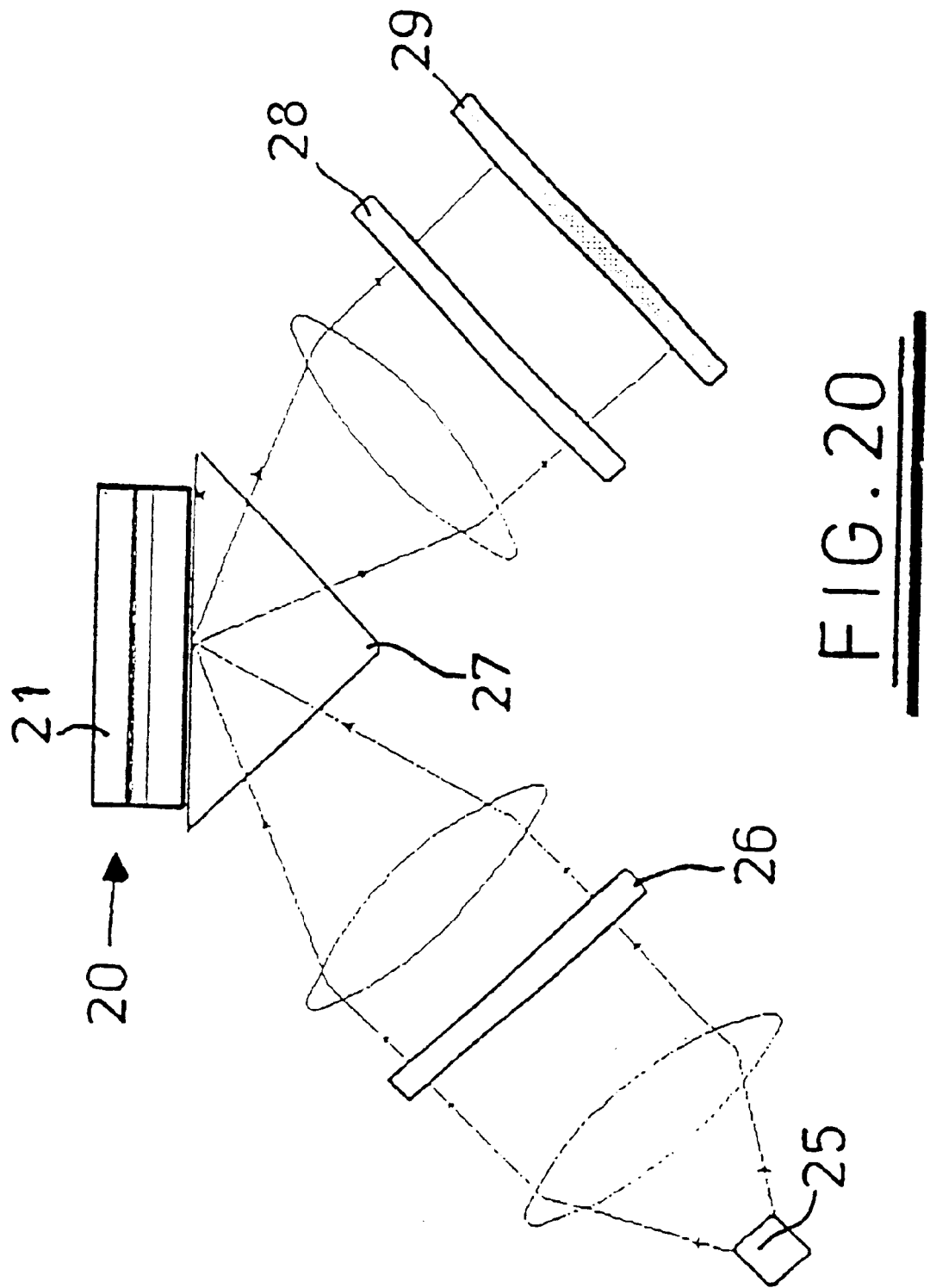
FIG. 20 is a graph illustrating the confinement of an optical mode within a waveguide structure corresponding to that illustrated in FIG. 19.

FIG. 20 shows an optical sensing apparatus which utilises the waveguide 20 illustrated in FIG. 19. The construction of the apparatus is based upon the construction of the known resonant mirror biosensor (see Cush, R. et al (1993) The resonant mirror, *Biosensors & Bioelectronics*, 8, 347–353). The apparatus comprises a source 25 which produces a beam of light at a known wavelength. The beam is collimated, and then polarised by a polariser 26 to provide equal proportions of TE and TM excitation before being focused into a prism 27. The beam is coupled from the prism 27 into the waveguide 20 via leakage of the modes of the waveguide 20. Efficient coupling into the sensing layer 21 of the waveguide 20 will occur only for certain angles of incidence where phase matching between the incident beam and resonant modes of the sensing layer 21 is achieved. The angle at which the beam is incident upon the prism 19 is scanned continuously through a predetermined range, which is chosen to include those angles needed to excite resonant modes of the core layer. An alternative arrangement of apparatus couples incident light to the waveguide 19 in a wedge shape, thereby providing light simultaneously at a range of incident angles which include all angles of interest.

The incident angle which will provide efficient coupling to the sensing layer 21 of the waveguide 20 (i.e. the angle which will excite a mode of the waveguide 20) is dependent upon the refractive index of the sensing layer 21 and on the refractive index of the substrate 24 and prism 27. Molecular interactions occurring within the sensing layer 21 will modify the refractive index of the core 21 and thereby change the incident angle required for efficient coupling. This change in refractive index may be monitored by measuring changes in the angle which provides efficient coupling.

Light which is coupled into the sensing layer 21 propagates a short distance along it before coupling back into the prism 27. Light emitted from the prism 27 may be collimated and then caused to pass through an analyser 28 comprising a polariser set at 45° to the axes of polarisation of the TE and TM components of the light and a quarter-wave plate. A detector 29 measures the position of fringes produced by interference between the TE and TM components of the light passed by the analyser 28.

The phase of light reflected by the waveguide 20 undergoes a full 2π change on passing through a resonance peak (i.e. an angle of incidence which provides efficient coupling to the sensing layer 21). It is the position of this phase step which is monitored to measure changes in the optical properties of the sensing layer 21. The resonant optical modes for TE and TM excitation are widely separated. As the angle of the incident light approaches the angle needed to excite, for example, a resonant TE mode, the phase of light coupled from the core layer will be shifted, and will pass through a maximum phase shift of π at the resonance peak. Light which is coupled to a TM mode of the sensing layer 21 at the same angle of incidence will not pass through a resonant mode, and interference at the analyser between light coupled from the TE and TM modes of the sensing layer 21 will be modified by the π phase shift of the TE mode, thereby indicating the presence of the TE resonance.

The ARROW waveguide is advantageous over known optical sensing apparatus in that the resonant modes of the waveguide 20 are almost wavelength insensitive, thereby removing the need for coherent sources of light to be provided with wavelength stabilisation mechanisms, The source 25 used by the ARROW waveguide may be either a laser a light emitting diode or a white light source. The use of a light emitting diode (or a white light source), which produces light over a wider band of frequencies than would be produced by an equivalent laser, is made possible by the wavelength insensitivity of the ARROW structure of the waveguide 20. Light emitting diodes and other broad band sources are advantageous because they do not suffer from 'speckling', which degrades the performance of instruments that use diode lasers. The use of a white light source will allow the spectroscopic analysis of biological samples—something that is difficult or impossible to do with conventional waveguide sensors.

The ARROW waveguide is advantageous in that the method of excitation of modes of the ARROW waveguide and the method of detection is the same as is currently used for RM modes in the known resonant mirror biosensor (see Cush, R. et al). ARROW waveguides may therefore be used in place of resonant mirror waveguides in existing apparatus to obtain enhanced measurement sensitivity, without requiring a substantial change of instrumentation.

Figure 21:
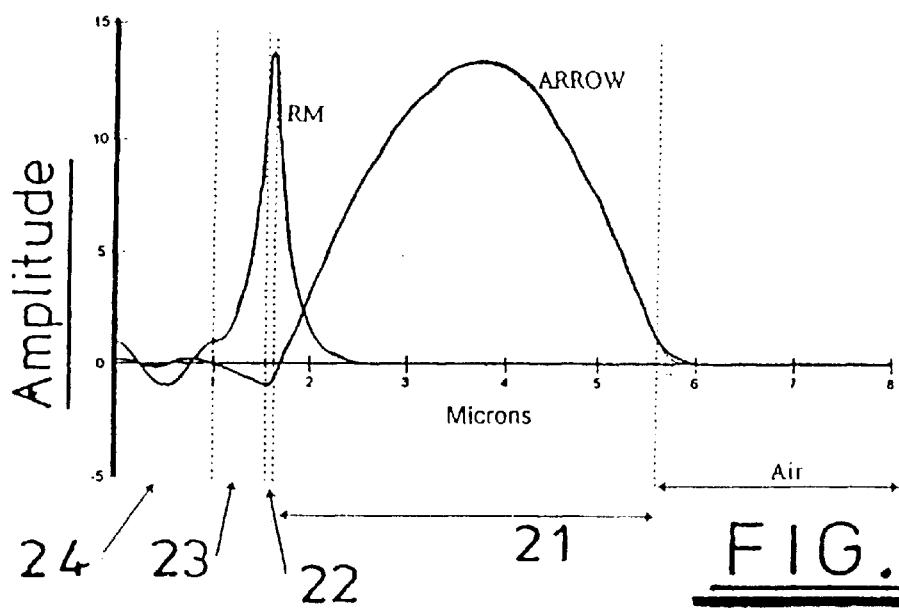
FIG. 21 is a schematic view from one side of an optical sensing apparatus.

FIG. 21 shows the real part of the amplitude of an optical field in the waveguide of FIG. 19. For comparison, two modes of the waveguide are shown: a resonant mode which occurs when the waveguide is acting as a resonant mirror, and a mode which occurs when the waveguide is acting as an ARROW waveguide. From FIG. 21 it can be seen that the overlap between the ARROW mode and the sensing layer 21 of gel is almost 100% whilst the overlap of the resonant mirror (RM) mode and the sensing layer 21 is about 40%. Any change in the refractive index of the gel of sensing layer 21 therefore has a greater effect on the ARROW mode than it does on the RM mode. The ARROW mode thus provides more sensitive detection than the RM mode, thereby providing the sensing apparatus with an enhanced performance when compared to RM sensors.

A further advantageous feature of the ARROW waveguide is that the leakage rate associated with the ARROW mode is much lower than that associated with the RM mode. This means that the ARROW mode resonances are much sharper than RM resonances (although the leakage rate of RM modes can be reduced by increasing the thickness of the silica layer 23).

The shift in the resonance angle of an ARROW resonance in response to a change in the refractive index of the core 21 was found to be 1.8 times greater than that of the corresponding RM resonance. With a tuned ARROW structure however, this figure may be increased to over 12. This enhanced shift of resonance angle, together with the relative sharpness of the ARROW modes, allows the sensing apparatus comprising an ARROW waveguide to resolve much smaller changes in the refractive index of a core layer than may be measured using conventional RM sensors.

A large overlap between the optical field and a core layer is a pre-requisite for efficient fluorescence and absorption measurements. The ARROW waveguide provides this large overlap. Since the overlap between the ARROW mode and the sensing layer 21 is almost 100%, the ARROW waveguide is particularly suited to fluorescence and absorption measurements.

The silica layer 23 in the waveguide of FIG. 19 is included so that both resonant mirror modes and ARROW modes of the waveguide 20 may be excited, thereby allowing comparisons of their properties. However, it is possible to fabricate an ARROW waveguide which does not include the silica layer 23. A waveguide of this form will be unable to support resonant mirror modes, but will support ARROW modes in the manner described above.

Although in general it is advantageous to produce waveguides which suffer as little absorption loss as possible, losses suffered by light in an ARROW waveguide mode may be of some use. Specifically, when a mode of an ARROW waveguide is excited, absorption suffered by the light in the waveguide mode will reduce the intensity of light coupled from the waveguide, when compared to light which is not coupled to a resonant mode of the waveguide. Thus, the presence of an ARROW mode will be indicated by a dip in the intensity of light coupled from a waveguide.

Since a mode may be detected as a change of intensity rather than as a change of phase, the angle of resonance may be determined without using the polariser 26 or analyser 28. The size of the dip in the intensity of light coupled from the waveguide is a function of the losses suffered by the mode in the waveguide, either by absorption or scattering. A disadvantage of absorption losses is that they will broaden resonances of an ARROW waveguide, thereby reducing measurement sensitivity.

Optical absorption losses may be induced by introducing absorbing dyes within the core and/or high index layers. Equivalent losses may be induced by providing a degree of roughness to one or more of the surfaces of the core or high index layers.

For a given set of waveguide parameters there is an optimal value of thickness of the high index reflector (layer 22 in FIG. 19), at which the leakage rate for a particular ARROW mode is a minimum. Minimising the leakage rate will reduce the width of the ARROW resonance to a minimum (the ARROW resonance is the range of angles of incidence which excite the ARROW mode). In many cases, it is advantageous to minimise the width of the ARROW resonance, since this will maximise measurement sensitivity.

Figure 22:
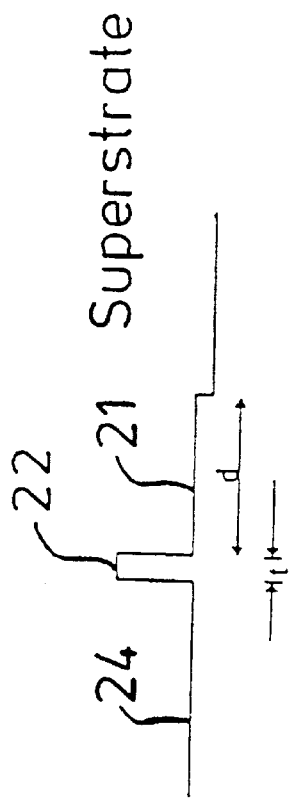
FIG. 22 is a refractive index profile of a waveguide structure.

A simple ARROW structure with a refractive index profile is shown in FIG. 22. The reference numerals of FIG. 22 correspond with the reference numerals applied to the structure shown in FIG. 19. For a structure of this type, the value of the optimum thickness, t, of the high-index reflector layer is given to a good approximation by:

$$t = \frac{(2N+1)\lambda}{4n_2}\left[1 - \left(\frac{n_1}{n_2}\right)^2 + \frac{\lambda^2}{4n_2^2 d^2}\right]^{-\frac{1}{2}}$$

N: zero or a positive integer

λ: free-space wavelength n1: refractive index of the core (guiding layer)

n2: refractive index of the high-index reflector layer d: thickness of the core (guiding layer)

Figure 23:
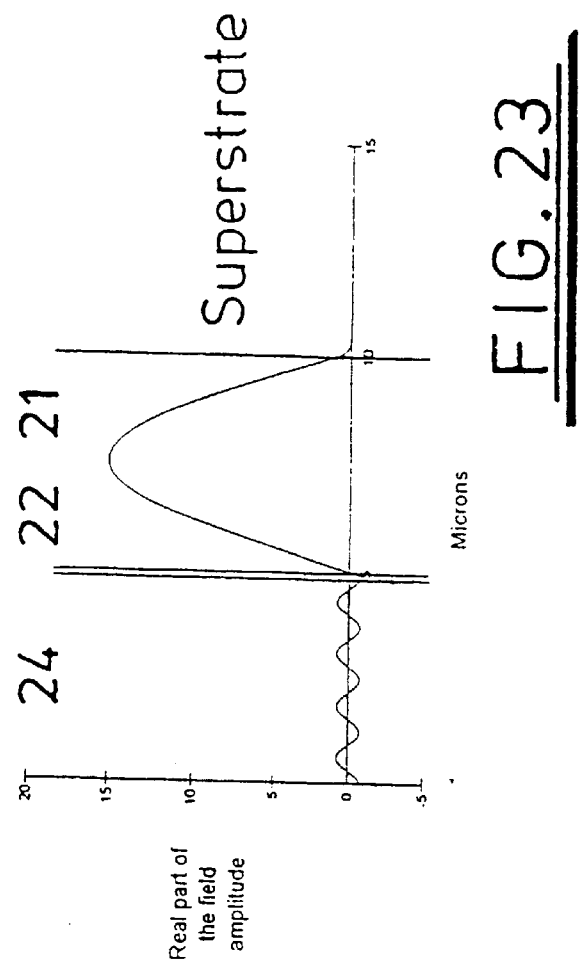
FIG. 23 is a graph illustrating the confinement of an optical mode within a waveguide structure corresponding to that illustrated in FIG. 22.

For the simple ARROW waveguide shown, this formula gives a good approximation to the optimum value of t, i.e. the value that results in a minimum leakage rate. A fundamental mode of a simple ARROW structure with the refractive index profile shown in FIG. 22 is illustrated in FIG. 23.

However, because the structure of ARROW sensors will not generally be as simple as that shown in this example, the value of t obtained by this formula can be taken as a rough guide only. To determine the optimum value of the reflector thickness for any general ARROW structure, the ARROW mode index may be numerically determined, e.g. by the transfer matrix method. The set of waveguide parameters that give the lowest leakage rate can then be determined.

In an alternative configuration of waveguide, the thicknesses and refractive indices of the high index layer 22 and the substrate 24 is selected to act as a Fabry-Perot resonator at resonant wavelengths (i.e. the thickness of the high index layer 22 is a multiple of the wavelength of light coupled to the waveguide, such that a maximum or near-maximum leakage of the optical mode occurs). This is in contrast to the design of ARROW waveguides, in which the structure is chosen such as to minimise the leakage of the optical mode. The waveguide configuration, referred to hereafter as a ROW waveguide provides strong confinement of light in the sensing layer 21.

A feature of suitably tailored ROW waveguides is that the mode index is a strong function of the refractive index of the sensing layer 21. The mode index of the sensing layer 21 is generally referred to as A, and the refractive index of the sensing layer 21 is generally referred to as 'n'. In ARROW waveguides, the quantity dβ/dn is approximately 1.0. However, in properly tailored ROW waveguides, dβ/dn may be significantly larger than 1.0. In other words, a change of the refractive index of the sensing layer 21, for example as the result of a molecular interaction, will in general lead to a larger change in the optical properties of the guided mode than would be seen in an ARROW waveguide.

Figure 24:
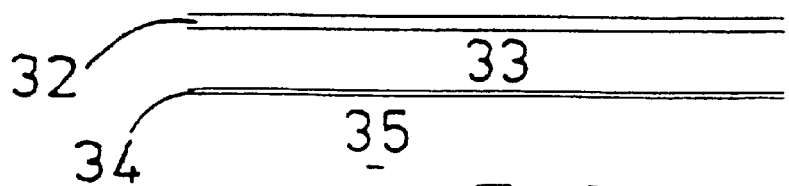
FIG. 24 is a schematic view from one side of a waveguide structure.

A drawback or ROW waveguides is that the mode index of ROW modes is a strong function of not only the refractive index of the sensing layer 21, but also of the refractive index and thickness of all other regions of the waveguide structure. Fabrication tolerance is therefore much stricter for ROW waveguides than it is for ARROW waveguides. Another drawback of ROW modes is that the mode index is a function of optical wavelength, and monochromatic optical excitation of ROW modes is this usually necessary. The main advantage of ROW waveguides is that the enhancement in sensitivity to changes of optical properties of a sensing layer 21 can be very large. In the ROW structure used as an example below, the value of dβ/dn is modest (approximately 1.09, compared with approximately 1.0 for ARROW waveguides). With suitable design, this value can be much higher A ROW waveguide structure is illustrated in FIG. 24. The structure comprises the following layers:

| Layer Reference No. | Region | Refractive index | Thickness (microns) |
|---|---|---|---|
| 30 | Superstrate | 1.00 | |
| 31 | Sensing layer | 1.347 or 1.3471 | 4.0 |
| 32 | Silicon nitride | 2.00 | 0.17 |
| 33 | Silica | 1.47 | 1.0 |
| 34 | Metal | 0.13–i3.16 | 0.015 |
| 35 | Substrate | 1.72038 | |

The waveguide structure shown in FIG. 24 has been computer modelled and found to operate as a ROW waveguide for light of 660 nm. When the refractive index of the sensing layer 31 is 1.3470, the real part of the mode index of the $TE_2$ is 1.344562. When the refractive index of the sensing layer 31 is 1.3471, the real part of the mode index of the $TE_2$ is 1.344671. This gives a value of dβ/dn= 1.09.

The metal layer 34 is included in the waveguide structure merely to provide optical loss and thereby allow the modes to be detected as dips in the intensity of reflected light. The ROW waveguide structure in general does not require a layer of metal.

Figure 25:
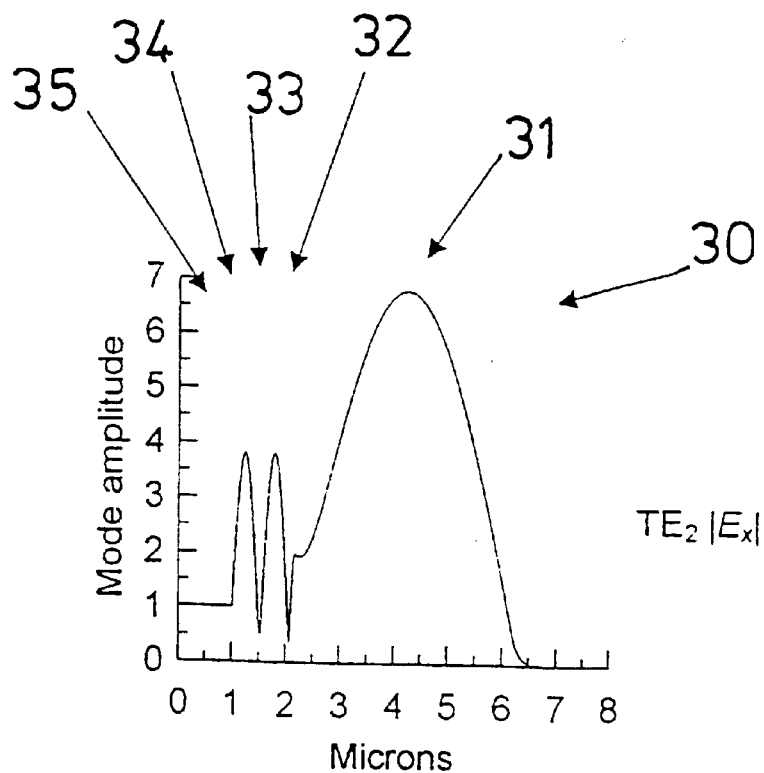
FIG. 25 is a graph illustrating the confinement of an optical mode within a waveguide structure corresponding to that illustrated in FIG. 24.

A mode profile of the $TE_2$ ROW mode is shown in FIG. 25.

The preceding discussion and the following discussion of ARROW waveguide structures may be applied, with relevant change, to ROW waveguide structures.

A broad resonance may be obtained from an ARROW structure by detuning the waveguide structure from the optimal ARROW configuration. This can be done by adjustment of any one or any combination of the following parameters: thickness of the high index layer, refractive index of the high index layer, refractive index of the substrate, refractive index of the sensing layer, thickness of the sensing layer, wavelength of the incident light.

Figure 26:
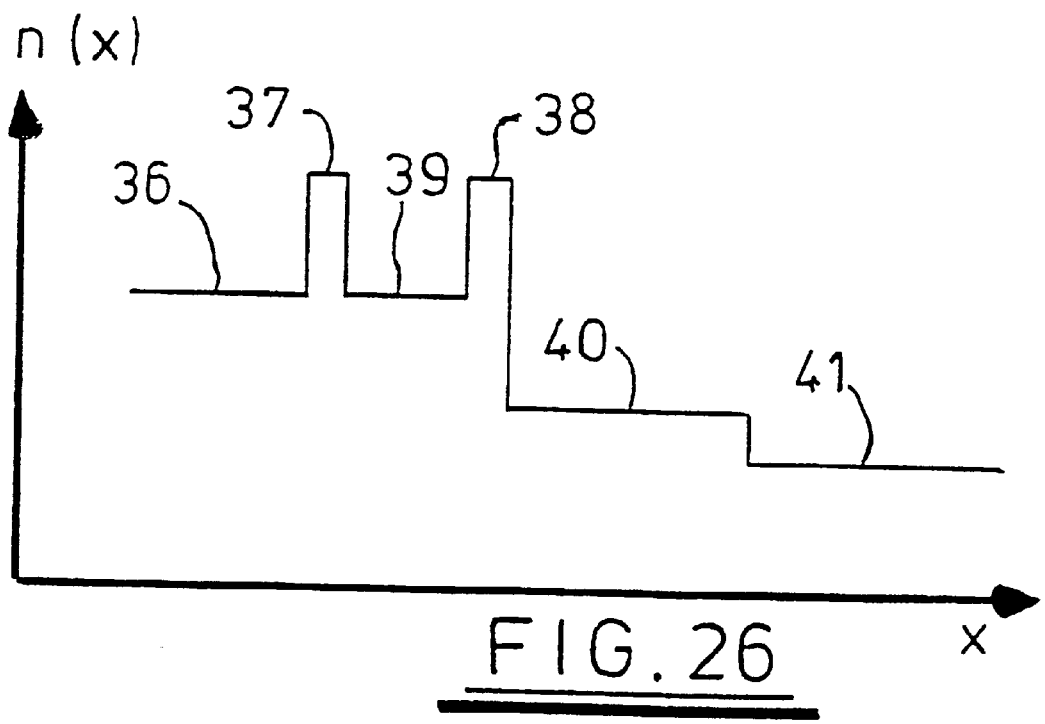
FIG. 26 is a refractive index profile of an alternative waveguide structure.

If, on the other hand, it is required that the ARROW resonance be sharper than that obtained using the optimal structure, further high index reflector layers may be included in a waveguide. Any number of high index reflector layers may be included in a waveguide structure. The refractive index profile of an ARROW waveguide which includes two high refractive index layers is shown in FIG. 26. The waveguide comprises a substrate 36 on top of which is provided two high refractive index layers 37, 38 separated by a spacer layer 39. A sensing layer of gel 40 is located on top of the uppermost high index layer 38. An upper surface of the sensing layer 40 forms an interface with a superstrate 41 of, for example, air. The refractive indices and thicknesses of the various layers of the waveguide shown in FIG. 26 may be varied in order to achieve a desired sharpness of ARROW resonance. The thickness andlor the refractive index of the high index layers 37 and 38 need not be the same. The refractive index of the sensing layer 40 must be greater than that of the superstrate 41, but less than that of the high index layer 38.

Figure 27:
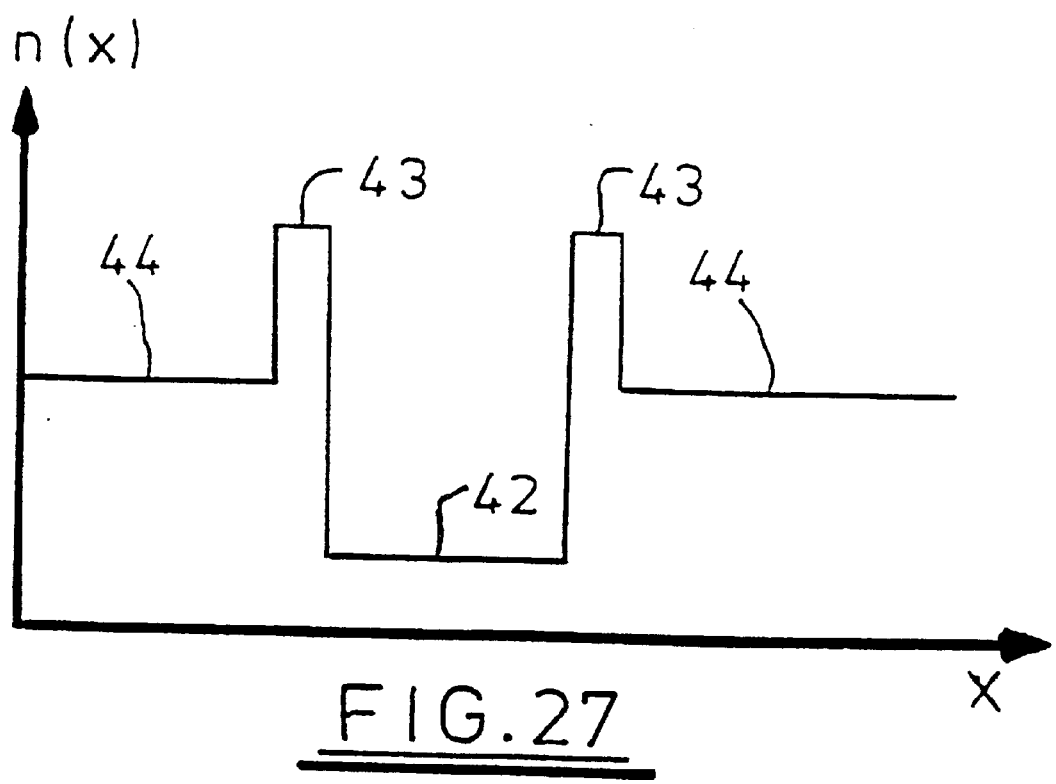
FIG. 27 is a refractive index profile of an alternative waveguide structure.

A further alternative form of ARROW waveguide structure is illustrated in FIG. 27. In this structure, a sensing layer 42 is bounded on either side by a high index layer 43, and a substrate 44. The structure illustrated in FIG. 27 will be referred to as symmetric, to differentiate it from those structures described above, which are grouped together under the description 'asymmetric'. In asymmetric ARROW waveguides, an uppermost surface of a sensing layer is bounded by a semi-infinite medium of lower refractive index (for example, air or water), which boundary provides total internal reflection. By contrast, a sensing layer 42 of a symmetric ARROW waveguide is bounded on two sides by a high refractive index layer 43 and a substrate 44, which form two ARROW structures, oriented such that modes in the sensing layer 42 are confined on both sides by ARROW confinement. The word 'symmetric' is intended to mean that the sensing layer 42 is provided on both sides with an ARROW structure, and does not require that the refractive indices of equivalent layers on either side of the sensing layer 42 are identical, or that the form of the ARROW structure on either side of the sensing layer 42 be the same.

A feature of symmetric ARROW sensors is that, as well as reflection of incident light, they also provide transmission of incident light. This is not the case with asymmetric ARROW sensors, in which transmission of light is inhibited by total internal reflection at an uppermost surface of a sensing layer. In contrast to this, ARROW modes in symmetric ARROW waveguides are leaky on both sides of the sensing layer 42. However, if desired, even a symmetric ARROW structure can be designed such that the ARROW modes are leaky on only one side. This may be achieved by reducing the refractive index of a superstrate of the structure to below the mode index of the ARROW modes of interest.

Transmission of light by a symmetric ARROW waveguide will occur only when light is incident on the waveguide at a resonant angle. The fact that a symmetric ARROW waveguide will transmit as well as reflect light greatly simplifies the measurement of the angle of incident light required to excite a resonance of the ARROW waveguide. An apparatus similar to that shown in FIG. 20 may be used with unpolarised light, thereby removing the need for polarisers at the input and output sides of the waveguide. At ARROW resonance angles, there is a dip in the reflectivity and a peak in the transmissivity of the waveguide, either of which may be detected easily. The position of the transmissivity peak is measured using a prism on the transmission side of the waveguide, and a detector.

A construction of symmetric ARROW waveguide with a sensing layer consisting of fluid may be used to detect refractive index changes in that fluid. Changes of the refractive index of the fluid are monitored using the techniques described above.

Alternative techniques for coupling light into an ARROW waveguide according to the invention include end-fire coupling and coupling via a grating etched on an interface within the waveguide.

Although the invention has been described by way of example in terms of simple ARROW waveguides, it will be clear to those skilled in the art that alternative more complicated configurations of ARROW waveguide may be fabricated which also allow an optical mode to be confined in, for example dextran gel or a polymer. Examples of such waveguides which may be used as part of an optical sensing apparatus are Directional-Couplers, Mach-Zehnder and other interferometric devices.

Figure 28:
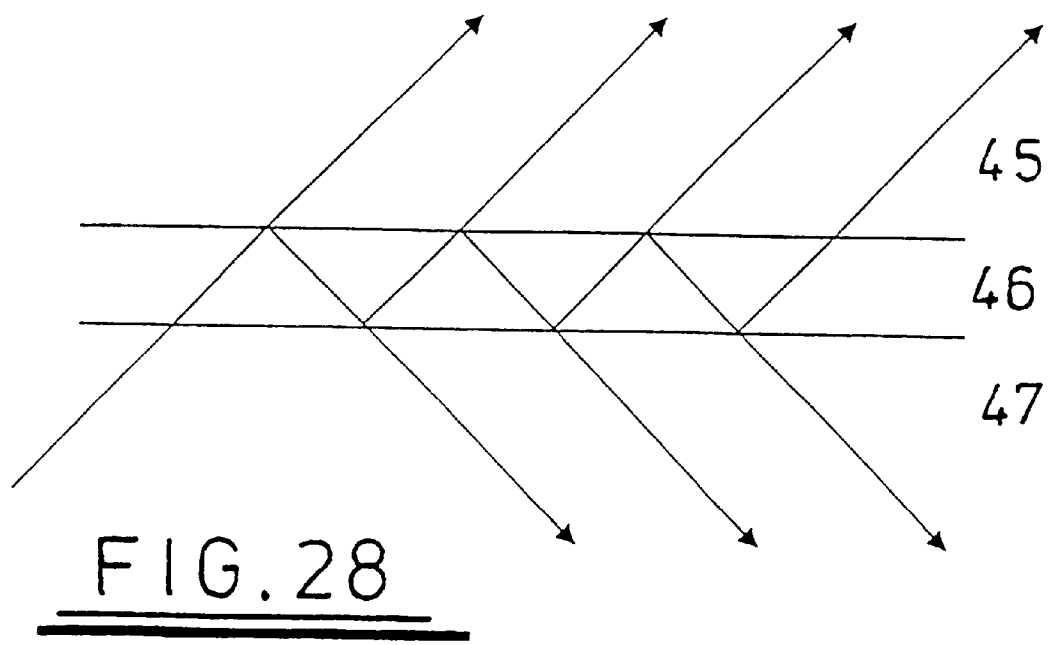
FIG. 28 is a schematic illustration of a light condenser waveguide structure.

FIG. 28 shows a waveguide according to the sixth aspect of the invention, which waveguide is referred to hereafter as a light condenser The light condenser comprises a high index superstrate 45, a low index sensing layer 46 and a high-index substrate 47. One possible configuration of a light condenser comprises a low index gel or other medium of interest with a refractive index of n=1.333, sandwiched between two layers of glass. The light condenser is a simple low-index waveguide with properties similar to ARROW waveguides.

Light is confined in the low-index guiding region of a light condenser by reflection from the index steps between the low-index sensing layer 46 and the high-index superstrate 45 and substrate 47. Because the refractive index of the superstrate 45 and substrate 47 is higher than that of the sensing layer 46, modes of the light condenser are leaky in nature. In other words the reflection from the core-cladding boundary is less than 100%, as indicated by light shown as arrows escaping through the superstrate 45 and substrate 47.

The guiding layer may be a polymer, water, gel or any other low-index material whose refractive index is to be monitored or in which fluorescence is to be excited.

The waveguide will function as a light condenser provided that the real part of the mode index of the light condenser mode is less than the refractive index of the superstrate 45 and substrate 47.

Figure 29:
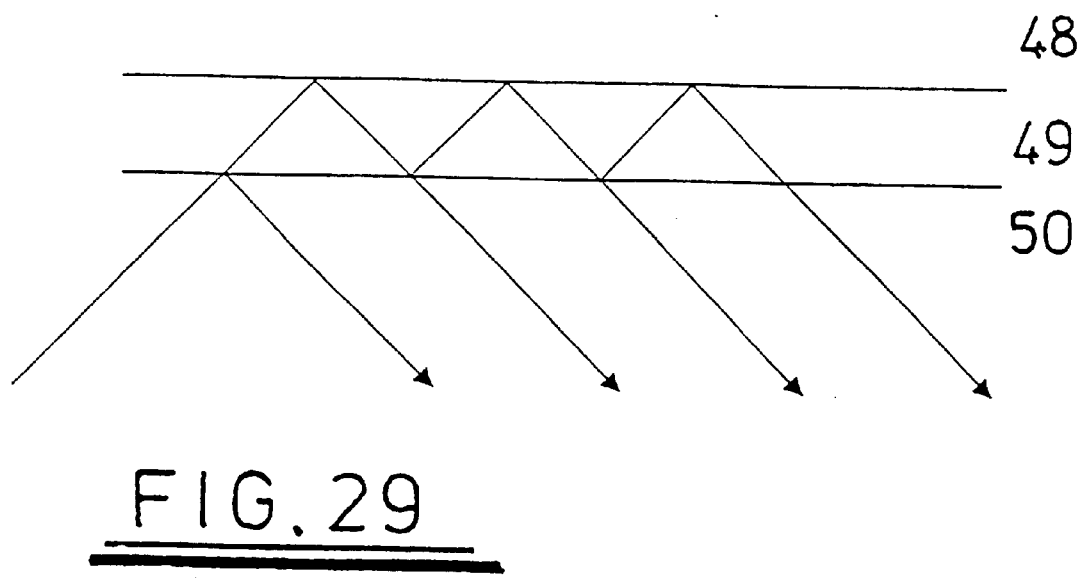
FIG. 29 is a schematic illustration of an alternative light condenser waveguide structure.

FIG. 29 shows a waveguide in which the refractive index of a substrate 48 is greater than the refractive index of a sensing layer 49, and the refractive index of the superstrate 50 is less than the refractive index of the sensing layer 49. Light is confined at the interface between the sensing layer 49 and the substrate by an index step, as described in relation to FIG. 28. Light is confined at the interface between the sensing layer 49 and the superstrate 48 by conventional total internal reflection. A waveguide of this type will be referred to as an asymmetric light condenser. In the asymmetric light condenser the real part of the mode index of a light condenser mode of interest is generally greater than the refractive index of the superstrate 48.

The waveguide will function as a light condenser at the interface between the sensing layer 49 and the substrate 48, provided that the real part of the mode index of the light condenser mode is less than the refractive index of the substrate 48.

The method of excitation of light condenser modes is the same as that described in relation to ARROW modes, and may utilise for example prism coupling, grating coupling or end-fire coupling.

The light condenser does not generally require lateral mode confinement, since light coupled to the light condenser is collimated. Where lateral confinement is required, this may be provided by etching into a substrate or superstrate a channel for receiving a sensing medium.

The light condenser waveguide may be fabricated from injection moulded plastic. A coupling prism may be formed together with the light condenser during fabrication. Electrodes, if required, may also be formed together with the light condenser during fabrication.

The light condenser waveguide may be used in the measurement of fluorescence (by including a fluorescent species in the sensing layer).

Figure 30:
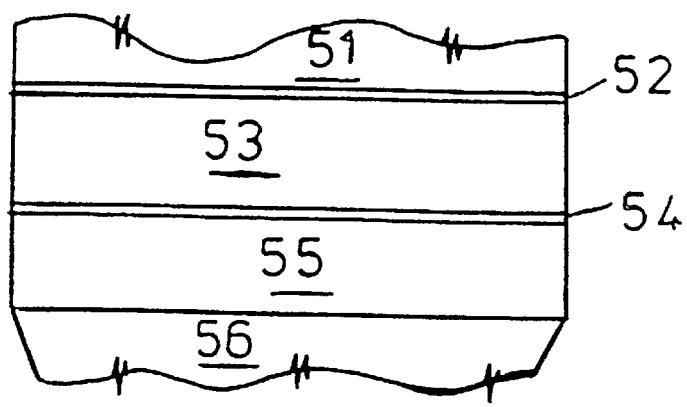
FIG. 30 is a schematic view from one side of a waveguide structure.

FIG. 30 shows a resonant mirror waveguide structure designed to operate at a wavelength of 0.66 microns, and designed to provide a measurement and a reference for that measurement. The waveguide structure comprises a sample 51 provided as a sensing layer on top of a thin layer of silicon nitride 52 (80 nm), which in turn is located on top of a thick layer of silica 53 (500 nm). The silica layer is located on a second thin layer of silicon nitride 54 (100 nm), which is located on a second thick silica layer 55 (500 nm). The entire structure is located on a substrate 56 (the undersides of which are angled to form a prism). The illustrated waveguide structure essentially comprises a first resonant mirror structure located on top of a second resonant mirror structure. The sensing layer may be low index dextran gel, or may be any other medium capable of supporting biological or chemical interactions, for example sample separation, antibody-antigen interactions, etc.

Figure 31:
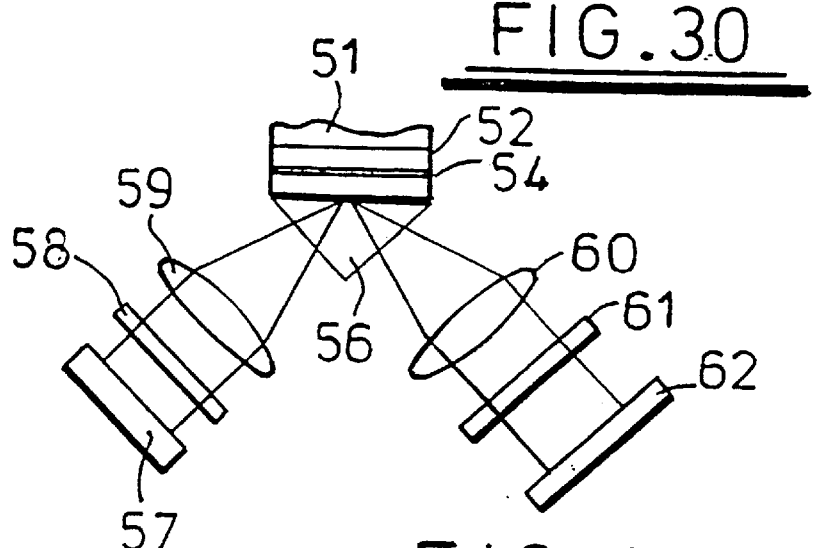
FIG. 31 is a schematic illustration of an optical sensor incorporating the waveguide of FIG. 30.

An optical sensor according to the invention is shown in FIG. 31. The sensor is similar to existing apparatus which is used to perform resonant mirror measurements and surface plasmon resonance measurements but modified to incorporate the waveguide structure of FIG. 30. The apparatus according to the invention comprises a light source 57 which produces a beam of light at a known wavelength. A polariser 58 is arranged to provide equal proportions of TE and TM excitation, and a lens 59 focuses the beam to a fan-shape. The beam is directed into a prism 56 which forms part of the waveguide. Although the prism 56 is shown as being triangular, it could be of any suitable shape (for example rectangular), and other forms of substrate may be used. Because the beam is directed towards the waveguide as a fan, light is incident at the waveguide from a range of different angles. The incident light will either be coupled to two resonant mirror modes centred respectively on the layers of silicon nitride 52, 54 or will be reflected from the waveguide structure without being coupled to a resonant mirror mode. Light will be coupled from the prism 56 of the waveguide in the form of a fan, and, after passing through a collimating lens 60 and an analyser 61 (comprising a polariser and a quarter-wave plate), will be incident upon a detector 62. The detector 62 comprises an array of charge coupled devices (CCD's) which detect the intensity of light at different sections of the fan, i.e. at different incidence angles.

The phase of light coupled from the waveguide will undergo a full $2\pi$ change on passing through a resonance peak (i.e. an angle of incidence which provides efficient coupling to the modes centred on the layers of silicon nitride 52, 54). It is the position of these phase changes which is monitored to measure changes in the optical properties of the sample 51. The resonant mirror optical modes for TE and TM excitation are widely separated in incidence angle. As the angle of the incident light approaches the angle needed to excite, for example, a resonant TE mode centred on the first layer of silicon nitride 52, the phase of light coupled from the waveguide will be shifted, and will pass through a maximum phase shift of $\pi$ at the resonance peak. Light which is coupled to a TM mode of the same layer at the same angle of incidence will not pass through a resonant mode. The polariser 60 is arranged to mix light from the TE and TM modes, thereby providing interference which passes through a peak of intensity as the TE mode passes through resonance. The position of the peak of intensity is dependent upon the optical properties of the waveguide structure.

The CCD array of the optical sensor may be replaced by a pair of photo-diodes (not shown) mounted so as to be capable of translation in a direction perpendicular to the direction of the light reflected from the waveguide. In use the photo-diodes would be positioned where peaks of intensity occurred, and would be translated to follow the peaks of intensity during an experiment, thereby allowing measurement of the degree of movement of those peaks of intensities.

A It will be appreciated that the combination of the light source 57 and lens 59 of FIG. 31 may be replaced by a collimated light source, mounted on a swinging arm. The arm would be swung through a required range of angles to produce illumination at the waveguide similar to the fan of light shown in FIG. 31. The lens 59 would not be required by the swinging arm arrangement.

The lens 60 may be removed from the apparatus without significant loss of performance.

Since the waveguide structure comprises two resonant mirror waveguides, a first angle of incidence will excite a mode centred on the first layer of silicon nitride 52 (i.e. a mode of the first resonant mirror), and a second angle of incidence will excite a mode centred on the second layer of silicon nitride 54 (i.e. a mode of the second resonant mirror).

Figure 32:
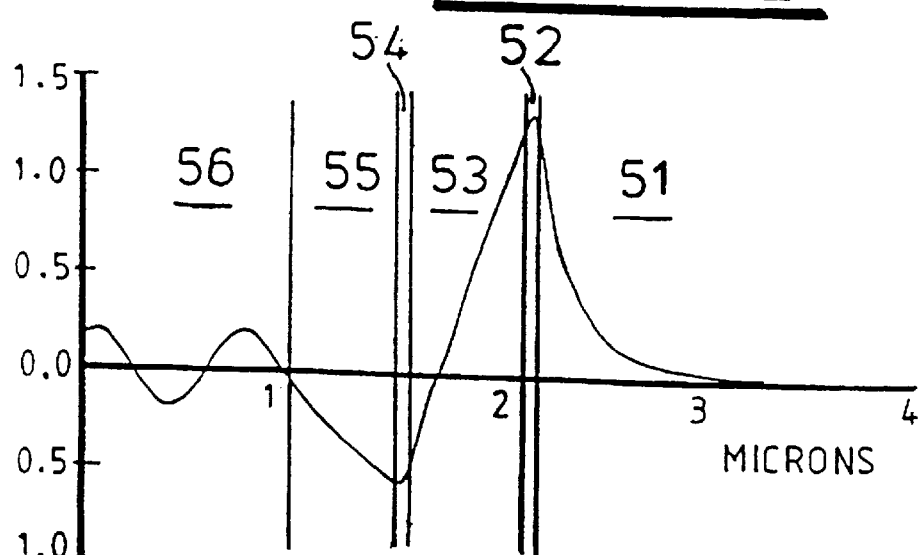
FIG. 32 is a diagram showing a first mode supported by the waveguide structure of FIG. 30.
Figure 33:
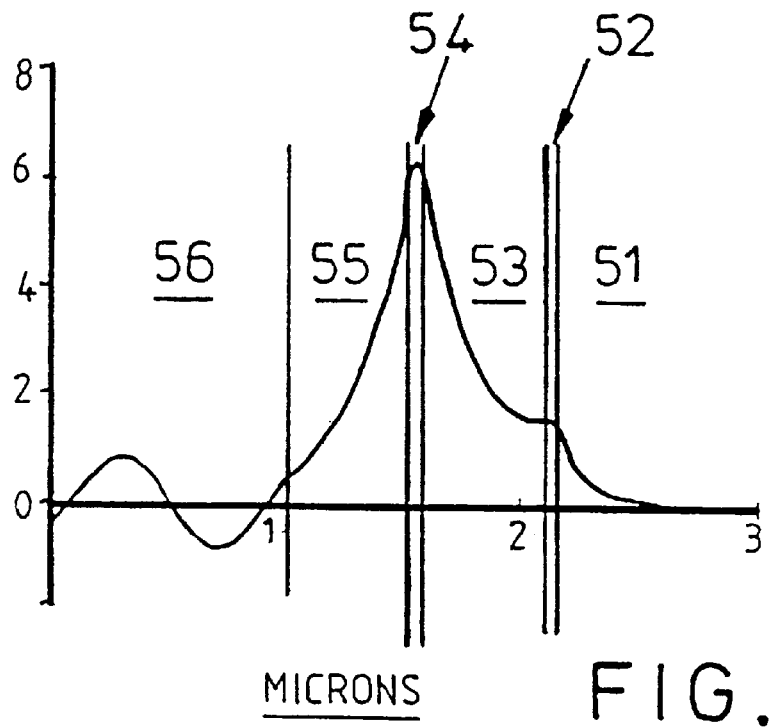
FIG. 33 is a diagram showing a second mode supported by the waveguide structure of FIG. 30.

FIGS. 32 and 33 illustrate optical fields associated with modes centred respectively on the first and second silicon nitride layers (52, 54) of the waveguide structure of FIG. 30 (the reference numerals are as used in FIG. 30). A significant fraction of the mode illustrated in FIG. 32 extends into the sensing layer 51 of the structure, and this mode will therefore be affected by changes of the optical properties of the sensing layer 51 (this mode will be referred to as the measurement mode). In contrast, only a very small proportion of the mode illustrated in FIG. 33 extends into the sensing layer 51, and this mode will be largely unaffected by changes of the optical properties of the sensing layer 51 (this mode will be referred to as the reference mode).

Figure 34:
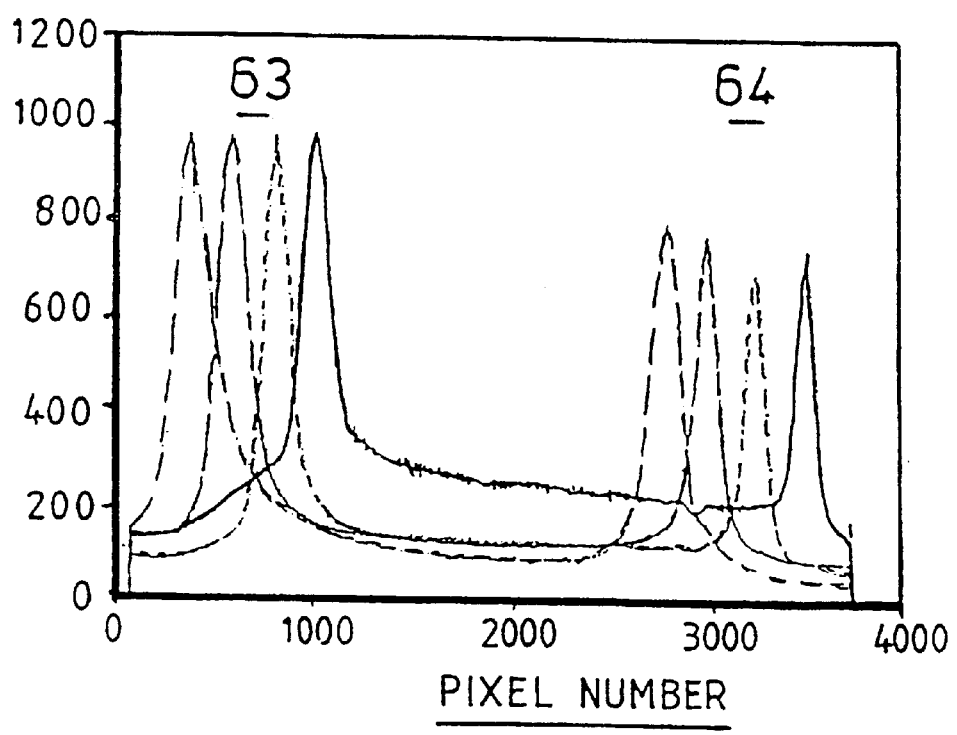
FIG. 34 is graph representing a series of outputs from the optical sensor shown in FIG. 31.

Using the structure of FIG. 30 it is possible to differentiate between changes in optical properties of the sensing layer 51, and unwanted optical effects such as any variation of the wavelength of light incident on the waveguide structure. For example, if the wavelength of incident light was to change, the angles of incidence required to excite both the measurement and reference modes would be altered, and the positions of the corresponding measurement and reference peaks detected by the CCD camera would be altered. The change in position of the reference peak is determined, and subtracted from the position of the measurement peak to remove the effect of the wavelength change from the measurement. This is illustrated in the experimental result shown in FIG. 34. The peaks on the graph are the recorded positions of outputs from an optical sensor incorporating the waveguide structure shown in FIG. 30, for four different wavelengths of incident light. The peaks 63 at the left-hand end of the graph are measurement peaks, and the peaks 64 to the right-hand end of the graph are reference peaks. From FIG. 34, it is clear that both the measurement and reference modes (and the positions of the corresponding peaks) are affected similarly by the changes of wavelength.

Figure 35:
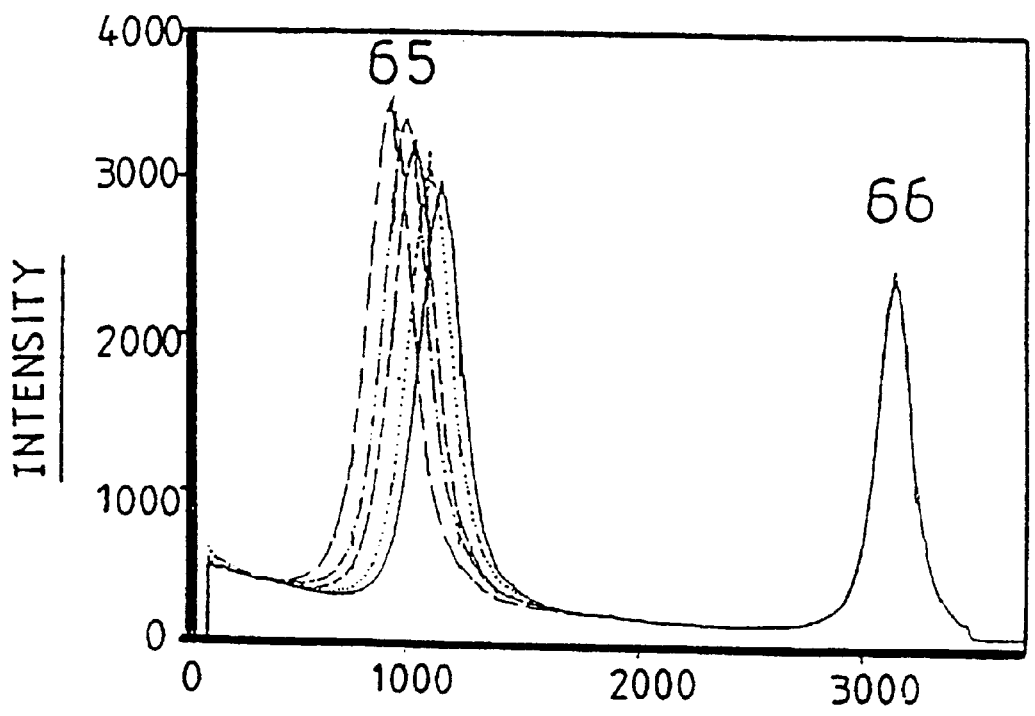
FIG. 35 is graph representing a further series of outputs from the optical sensor shown in FIG. 31.

In contrast, a change of the refractive index of the sample comprising the sensing layer 51 will significantly affect only the mode shown in FIG. 32. This is illustrated in FIG. 35, where the positions of the measurement peaks 65 to the left-hand end of the graph vary as the refractive index of the sample comprising the sensing layer 51 changes, and the reference peaks 66 to the right-hand end of the graph are substantially unaffected.

The invention is advantageous because it removes the need for stabilisation of the wavelength of the incident light; the effect of wavelength variation being removed by comparison of the measurement and reference peaks. A further advantage of the invention is that measurements are unaffected by changes in the temperature of the waveguide structure. If the temperature of the waveguide structure was to change, this would affect the measurement and reference modes equally, and the effect of the temperature change would thus be eliminated by comparison of the measurement and reference peaks.

In the above description it has been assumed that effects which act on both the measurement and reference modes (for example a change of wavelength) will affect each mode equally. However, since the modes are not identical, each mode will in fact behave slightly differently. By calibrating the effect of wavelength and temperature variations when the sample comprising the sensing layer 31 is inactive, the accuracy of subsequent measurements may be maximised. In the alternative, doping may be introduced into the structure in such a manner as to ensure that measurement and reference modes have the same behaviour with respect to temperature and wavelength variations.

The thickness of the first layer of silica 53 (in the waveguide shown in FIG. 30) is importance to the operation of the invention. If this layer is too wide then the measurement mode will not be excited, and if the layer is too thin then the reference mode will extend too far into the sensing layer 51, and will not provide a reference substantially independent of the sensing layer 51. The thickness of the first silicon nitride layer 52 may be chosen to be slightly less than the thickness of the second silicon nitride layer 54. This is so that the first layer is slightly more 'leaky' than the second, thereby ensuring that a sufficient proportion of the measurement mode will penetrate into the sensing layer 51.

Figure 36:
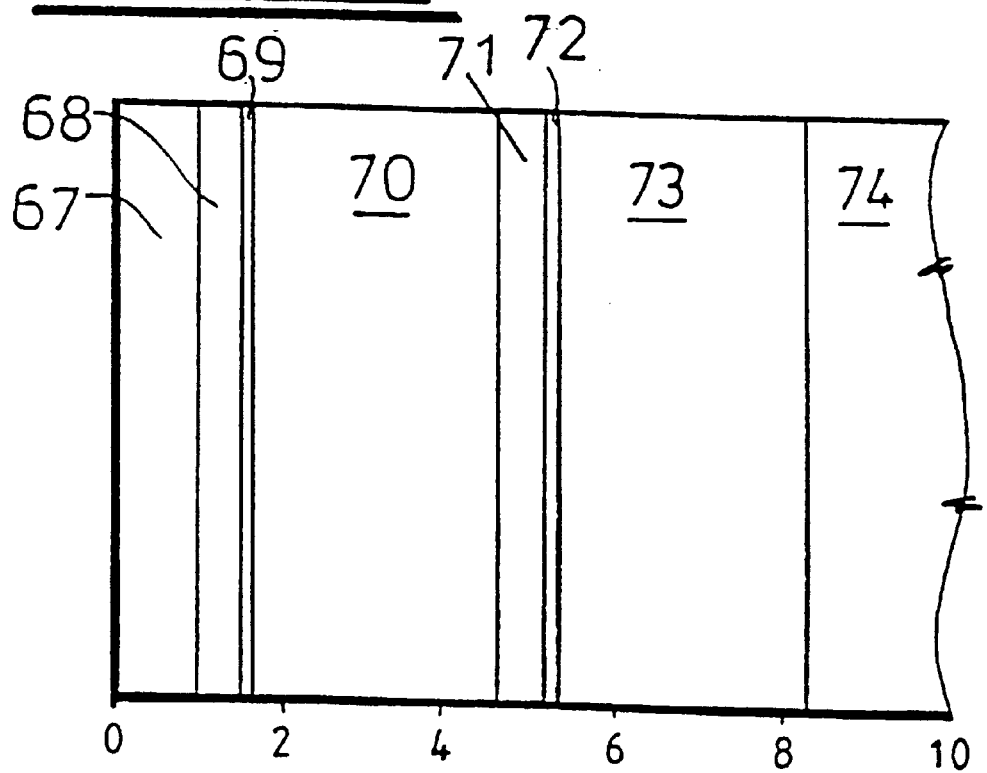
FIG. 36 is a schematic view from one side of a waveguide structure comprising part of an optical sensor.

FIG. 36 illustrates an anti-resonant reflecting optical waveguide (ARROW) biosensor, which is capable of supporting a reference mode which is unaffected by changes in the optical properties of a sample. The ARROW structure is comprised of the following layers:

| Layer Reference No. | Material | Refractive Index | Thickness (microns) |
| --- | --- | --- | --- |
| 67 | Substrate (SF 10) | 1.72038 | Semi-infinite |
| 68 | Silica | 1.47 | 0.55 |
| 69 | Silicon Nitride | 2.00 | 0.08 |
| 70 | High-Index Layer | 1.65 | 3.00 |
| 71 | Silica | 1.47 | 0.55 |
| 72 | Silicon Nitride | 2.00 | 0.08 |
| 73 | Dextran Gel | 1.35 | 3.00 |
| 74 | Water | 1.333 | Semi-infinite |

It will be understood that the above materials and thicknesses are given only as examples, and other materials of appropriate thicknesses may be used to construct a waveguide capable of supporting ARROW modes. In particular, the dextran gel is just one of many possible materials which may be used to support a sample of interest. The layer of substrate may be considered to be semi-infinite, and the substrate is shown as being 1 micron thick to allow a zero position to be defined.

Figure 37:
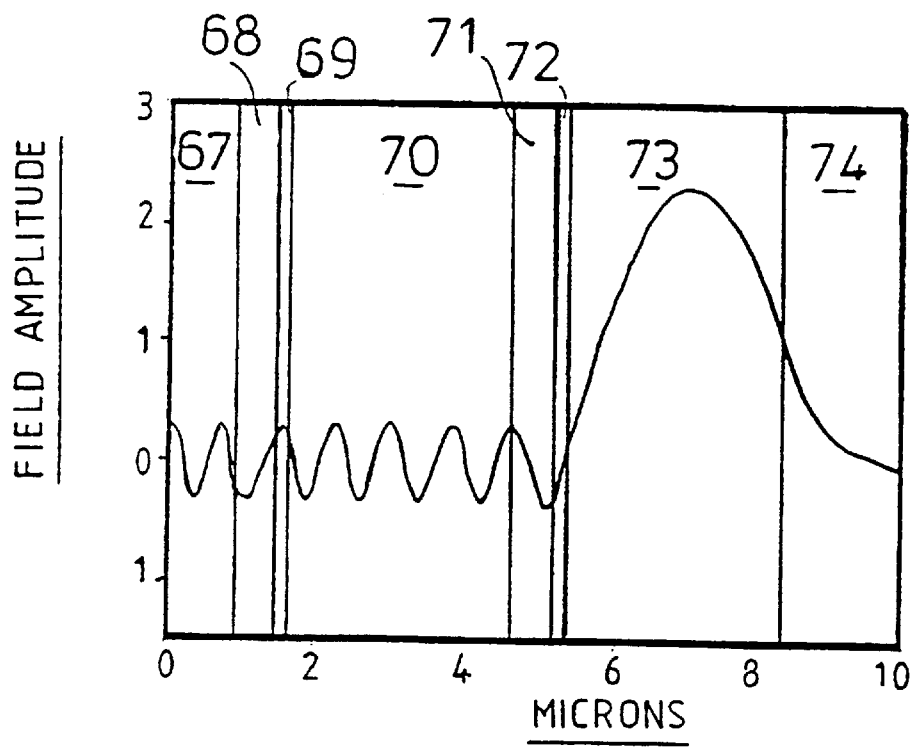
FIG. 37 is a diagram showing a first mode supported by the waveguide structure of FIG. 36.
Figure 38:
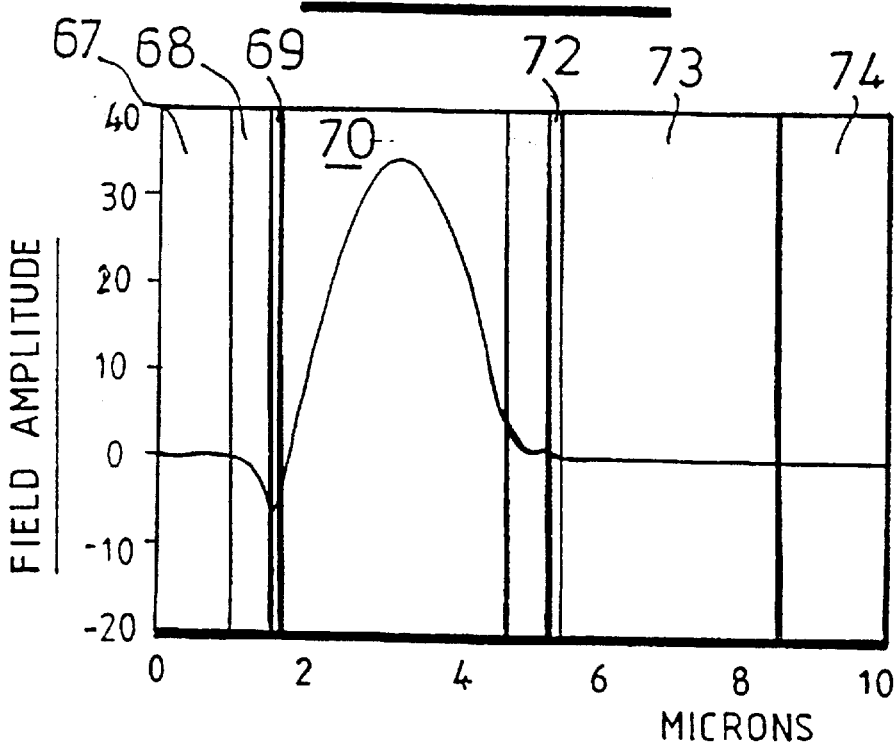
FIG. 38 is a diagram showing a second mode supported by the waveguide structure of FIG. 36.

FIGS. 37 and 38 respectively show first and second ARROW modes centred on layers 73 and 70 of the structure of FIG. 36. The modes are excited by directing incident light from an appropriate angle, in a manner analogous to that described above. The physics of ARROW waveguides is well known, and is described in the paper: Duguay el al, Appl. Phys. Lett., 49 (1986) 13–15. The reference mode of the ARROW waveguide (i.e. the second mode), as shown in FIG. 38, may be used to eliminate unwanted artifacts from a measurement of the optical properties of a sample, in the manner described above.

It will be understood by those skilled in the art that the waveguide structure illustrated in FIG. 36 may also be made to support resonant mirror modes. The silica layers 68, 71 are included in the waveguide to allow the resonant mirror modes to be supported. This particular waveguide is designed to support resonant mirror modes at a wavelength of 0.66 microns. A waveguide constructed without these layers would not support resonant mirror modes, but would still be capable of supporting ARROW modes.

Figure 39:
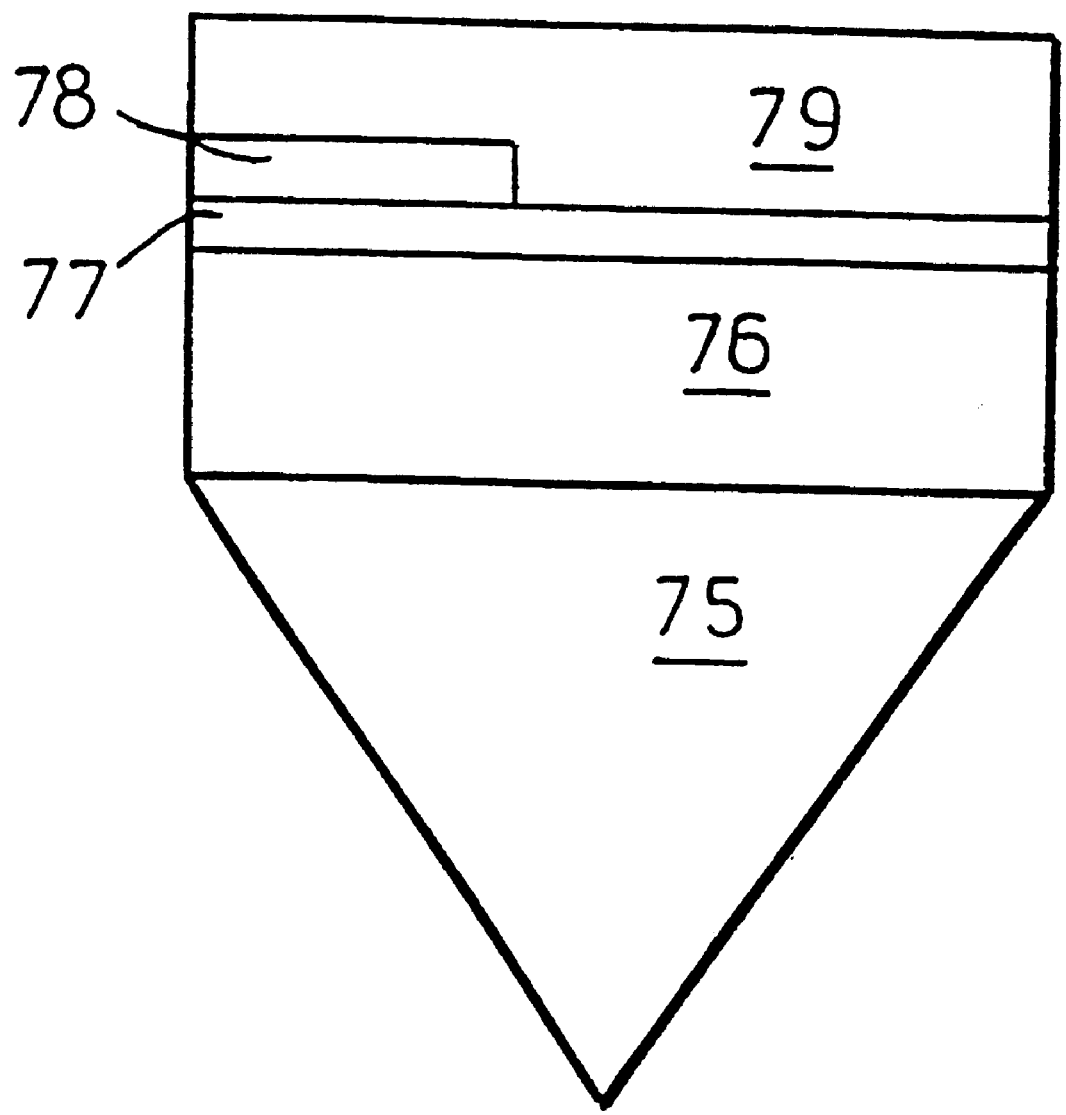
FIG. 39 is a schematic view from one side of a waveguide structure comprising part of an optical sensor.

FIG. 39 illustrates a further embodiment of the invention. A waveguide comprises a prism 75, a layer of silica 76 and a high index silicon nitride layer 77. A layer of chemically inert material 78 with a refractive index lower than that of the silicon nitride layer 77 is located at a left hand end of an upper surface of the silicon nitride layer 77, and a sample 79 is disposed as a sensing layer so as to cover the remaining upper surface of the silicon nitride layer 77 and an upper surface of the polymer layer 78.

In use, when a fan of light is coupled into the waveguide of FIG. 39, a mode centred on the silicon nitride layer 77 will be excited. At a left hand end of the waveguide the mode will extend into the polymer layer 78, but will not extend substantially beyond the polymer layer 78. At a right hand end of the waveguide the mode will extend into the sensing layer 79. Thus, the excited mode comprises two components which may be considered to be two modes, the left hand mode being substantially unaffected by changes of the properties of the sample (i.e. a reference mode) and the right hand mode being sensitive to changes of the properties of the sample (i.e. a measurement mode). The waveguide shown in FIG. 39 may be used with the apparatus shown in FIG. 31, as described above.

It will be understood that the layer of silicon nitride 77 could be replaced by a layer of any suitable material having a refractive index greater than that of the silica 76, the inert material 78 and the sensing layer 79. Similarly, the layer of silica may be replaced by any other suitable material. The chemically inert material 78 may be silicon, or alternatively a polymer chosen because it does not react to an analyte to be monitored may be used.

Figure 40:
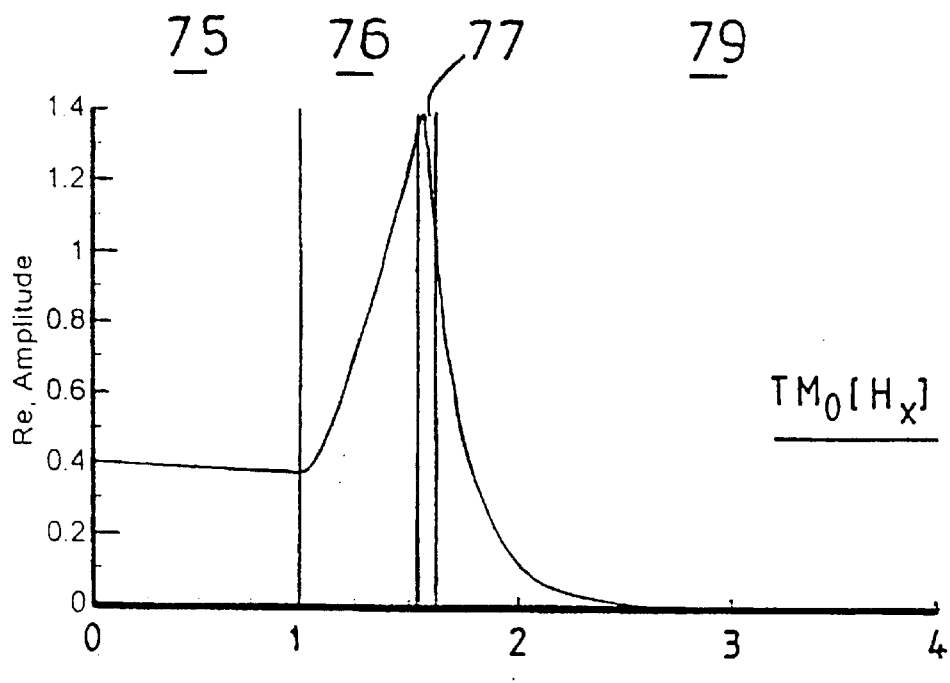
FIG. 40 is a diagram showing a first mode supported by the waveguide structure of FIG. 39.

FIG. 40 shows a first resonant mirror mode located at a right hand end of the waveguide structure of FIG. 39. A substantial proportion of the first mode extends into the sensing layer 79, and this mode will therefore be sensitive to changes of the optical properties of that layer (i.e. the first mode is a measurement mode).

Figure 41:
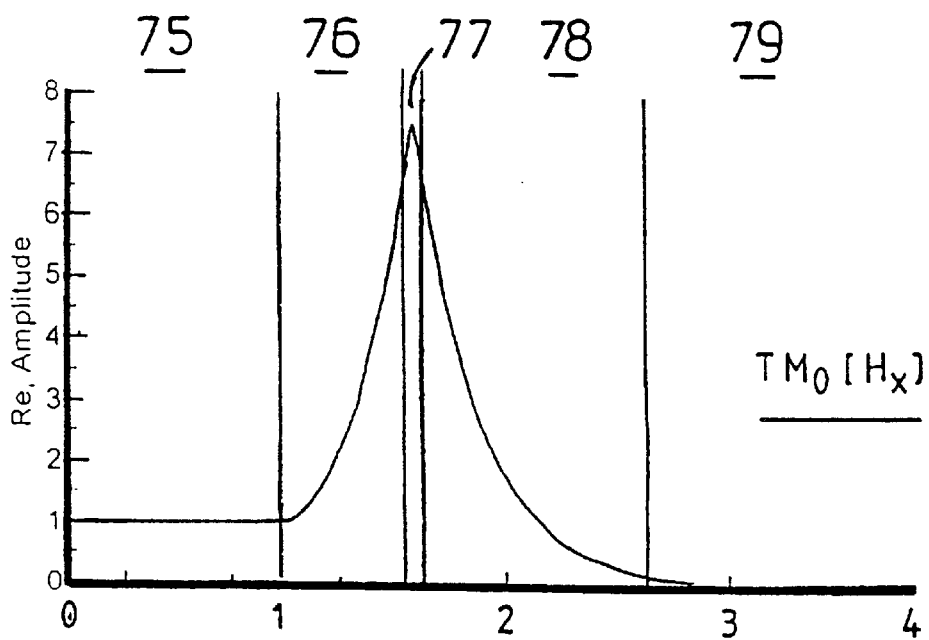
FIG. 41 is a diagram showing a second mode supported by the waveguide structure of FIG. 39.

FIG. 41 shows a second resonant mirror mode located at a left hand end of the waveguide structure of FIG. 39. Only a very slight proportion of the second mode extends into the layer of sensing material 79, and this mode will therefore be substantially unaffected by changes of the optical properties of that layer (i.e. the second mode is a reference mode).

The waveguide of FIG. 39 is advantageous over previously described embodiments because it has fewer layers and is therefore easier and cheaper to fabricate.

It is noted that the substrate of the above waveguide structures described in FIGS. 30, 36 and 39 (i.e. layers 56, 67 and 75) may be angled to form a prism, or may be provided with a planar base which is to be located upon a separate prism made from the same material as the substrate.

Each of the waveguide structures described in FIGS. 30, 36 and 39 may also be provided in what is known as a symmetric form. In each case the symmetric form comprises a central layer of sensing medium, with identical layers disposed on either side of the central layer, the layers on both sides being arranged as shown in FIGS. 30, 36 and 39. Light coupled to a symmetric waveguide will undergo reflection as described above, but will also be transmitted by that waveguide when a resonant mirror mode or ARROW mode is excited. The proportion of light reflected by the waveguide when a resonant mirror mode or ARROW mode is excited is reduced as a consequence of the transmission, and the presence of such a mode will therefore indicated by a dip in the intensity of light reflected by the waveguide. Symmetric arrangements of waveguides are thus advantageous because they allow the detection of resonant mirror modes or ARROW modes without the use of polarisers or wave-plates.

Detection of resonant mirror modes or ARROW modes may also be achieved by introducing absorption or scattering loss into the layer of sensing medium of the waveguide structures shown in FIG. 30, 36 or 39. In a waveguide of this type excitation of a resonant mirror mode or ARROW mode will lead to a reduction of the intensity of light reflected from the waveguide, due to losses occurring in the sensing medium. The presence of a resonant mirror mode or an ARROW mode will thus be indicated by a dip in the intensity of reflected light. The introduction of loss into the sensing medium is advantageous because it simplifies detection, as discussed above in relation to the symmetric waveguide form. It is noted that the presence of loss in the sensing medium will increase the range of incidence angles which are capable of exciting a resonant mirror mode or ARROW mode, thereby reducing experimental sensitivity.

The sensor waveguides described in relation to FIGS. 30 to 41 are similar in terms of dimensions and optical properties to sensor waveguides used in existing resonant mirror optical biosensing apparatus. A sensor waveguide as descried may therefore be introduced into existing biosensing apparatus with a minimal amount of modification. The temperature stabilisation and current stabilisation used by existing biosensing apparatus is not required when sensors according to the invention are used, and may be dispensed with, thereby reducing the complexity and cost of the apparatus.

It will be understood that the structures described in relation to FIGS. 30, 36 and 39 are concerned with providing waveguide structures having reference modes which are unaffected by changes of optical properties of a sample. The invention may be applied to other waveguide structures, and such applications will be apparent to those skilled in the art.

What is claimed is:

1. An optical sensor comprising a waveguide having a substrate, a layer of metal or metal alloy disposed on top of the substrate, and a medium disposed as a sensing layer on top of the layer of metal or metal alloy, the medium having optical properties which change if the medium is exposed to conditions to be sensed, the sensor further comprising means for directing light towards the layer of metal or metal alloy through the substrate over a range of incident angles, and detection means for detecting the intensity of light returned from the waveguide over a range of detection angles, the means for directing light being configured to direct light such that a leaky waveguide mode is excited within the sensing layer, and the means for detecting the intensity of light being arranged to detect variations with detection angle in the intensity of returned light resulting from the excitation of the leaky waveguide mode; characterised in that the waveguide is configured such that the overlap of the optical field with the layer of metal or metal alloy is less for light incident at an angle which results in excitation of a leaky waveguide mode than for light incident at an angle which does not result in excitation of a leaky waveguide mode, whereby the detected intensity peaks at a detection angle related to an incident angle which results in excitation of a leaky waveguide mode.

2. An optical sensor according to claim 1, wherein the substrate comprises a prism or grating for coupling light into the waveguide mode.

3. An optical sensor according to claim 1, further comprising a broad band optical source.

4. An optical sensor according to claim 3, wherein the optical source is a light emitting diode.

5. An optical sensor according to claim 1, wherein the detection means is a charge-coupled-device array (CCD) comprising cells of sufficiently small dimensions to allow resolution of the intensity variations resulting from the excitation of the waveguide mode.

6. An optical sensor according to claim 1, wherein the detection means is a single photo-diode arranged to be translatable across the light returned from the waveguide.

7. An optical sensor according to claim 1, wherein the thickness of the layer of medium is greater than 200 nanometers.

8. An optical sensor according to claim 1, wherein the thickness of the layer of medium is greater than 300 nanometers.

9. A method of optical sensing comprising providing a waveguide comprising a substrate, a layer of metal or metal alloy disposed on top of the substrate, a medium disposed as a sensing layer on top of the layer of metal or metal alloy, the medium having optical properties which change if the medium is exposed to conditions to be sensed, directing light towards the layer of metal or metal alloy through the substrate over a range of incident angles, and detecting the intensity of light returned from the waveguide over a range of angles, wherein the incident light is directed such that a waveguide mode is excited within the sensing layer, and variations in the intensity of returned light resulting from the excitation of the waveguide mode are detected; characterised in that the waveguide is configured such that the overlap of the optical field with the layer of metal or metal alloy is less for light incident at an angle which results in excitation of a leaky waveguide mode than for light incident at an angle which does not result in excitation of a leaky waveguide mode, whereby the detected intensity peaks at a detection angle related to an incident angle which results in excitation of a leaky waveguide mode.

* * * * *